(12) United States Patent
Hoeg et al.

(10) Patent No.: US 9,603,512 B2
(45) Date of Patent: *Mar. 28, 2017

(54) WIRELESSLY POWERED MEDICAL DEVICES AND INSTRUMENTS

(75) Inventors: Hans David Hoeg, Arcadia, CA (US); Charles E. Ankner, Santa Maria, CA (US); Ray Coussa, Goleta, CA (US)

(73) Assignee: Karl Storz Imaging, Inc., Goleta, CA (US)

(*) Notice: Subject to any disclaimer, the term of this patent is extended or adjusted under 35 U.S.C. 154(b) by 1212 days.

This patent is subject to a terminal disclaimer.

(21) Appl. No.: 12/545,567

(22) Filed: Aug. 21, 2009

(65) Prior Publication Data
US 2010/0179384 A1 Jul. 15, 2010

Related U.S. Application Data

(63) Continuation-in-part of application No. 12/425,869, filed on Apr. 17, 2009.
(Continued)

(51) Int. Cl.
| | | |
|---|---|---|
| *A61B 1/00* | (2006.01) | |
| *A61B 1/04* | (2006.01) | |
| *A61B 1/045* | (2006.01) | |

(52) U.S. Cl.
CPC .......... *A61B 1/042* (2013.01); *A61B 1/00006* (2013.01); *A61B 1/00009* (2013.01);
(Continued)

(58) Field of Classification Search
CPC ............ A61B 1/00016; A61B 1/00029; A61B 1/00059; A61B 1/042; A61B 1/045;
(Continued)

(56) References Cited

U.S. PATENT DOCUMENTS

| | | |
|---|---|---|
| 1,119,732 A | 12/1914 | Tesla |
| 6,092,722 A | 7/2000 | Heinrichs et al. |

(Continued)

FOREIGN PATENT DOCUMENTS

| | | |
|---|---|---|
| EP | 1868280 A2 | 12/2007 |
| JP | 11309156 A | 11/1999 |

(Continued)

OTHER PUBLICATIONS

Nakajima et al., Wireless Video Camera for Endoscope, May 2016, Phoenix Translations for USPTO, pp. 1- 20.*
(Continued)

*Primary Examiner* — John P Leubecker
*Assistant Examiner* — Arnaldo Torres Diaz
(74) *Attorney, Agent, or Firm* — Whitmyer IP Group LLC

(57) ABSTRACT

A medical device that is wirelessly powered by a resonant magnetic field, the device automatically coupling to a power transmitter in a control unit when brought within a threshold radius. In one embodiment, the control unit automatically identifies the medical device and automatically adjusts its settings to control the medical device, where the device and power transceivers may be provided detachable from either or both the endoscope/camera and camera control unit or may be provide integral to either one or both.

30 Claims, 23 Drawing Sheets

Related U.S. Application Data

(60) Provisional application No. 61/047,967, filed on Apr. 25, 2008.

(52) U.S. Cl.
CPC ...... *A61B 1/00016* (2013.01); *A61B 1/00029* (2013.01); *A61B 1/00036* (2013.01); *A61B 1/041* (2013.01); *A61B 1/045* (2013.01); *A61B 1/00027* (2013.01); *A61B 1/04* (2013.01); *A61B 2560/0214* (2013.01)

(58) Field of Classification Search
CPC ....... A61B 1/06; A61B 1/0676; A61B 1/0684; A61B 1/00064; A61B 1/0006; A61B 1/0002; A61B 1/00055; A61B 1/00128; A61B 1/05; A61B 1/00034; A61B 2560/0214; A61B 2560/0276; G02B 23/2484; H04N 5/23203; H04N 5/23209; H04N 7/181; H04N 5/2252; H04N 2005/2255
USPC ............ 600/109, 112, 177; 307/104; 348/65
See application file for complete search history.

(56) References Cited

U.S. PATENT DOCUMENTS

| | | | |
|---|---|---|---|
| 6,184,651 B1 | 2/2001 | Fernandez et al. | |
| 6,569,163 B2 | 5/2003 | Hata et al. | |
| 6,597,076 B2 | 7/2003 | Scheible et al. | |
| 7,042,196 B2 | 5/2006 | Ka-Lai et al. | |
| 7,668,450 B2 | 2/2010 | Todd et al. | |
| 8,035,255 B2 | 10/2011 | Kurs et al. | |
| 8,194,122 B2 | 6/2012 | Amling et al. | |
| 8,545,396 B2 | 10/2013 | Cover et al. | |
| 2002/0007111 A1* | 1/2002 | Deckert et al. | 600/177 |
| 2002/0118004 A1 | 8/2002 | Scheible et al. | |
| 2003/0174205 A1* | 9/2003 | Amling et al. | 348/65 |
| 2004/0236193 A1* | 11/2004 | Sharf | 600/302 |
| 2005/0064815 A1 | 3/2005 | Kanazawa | |
| 2005/0065407 A1 | 3/2005 | Nakamura et al. | |
| 2005/0080318 A1 | 4/2005 | Squicciarini | |
| 2005/0080342 A1 | 4/2005 | Gilreath et al. | |
| 2005/0154294 A1* | 7/2005 | Uchiyama et al. | 600/420 |
| 2005/0177024 A1* | 8/2005 | Mackin | 600/120 |
| 2006/0173245 A1* | 8/2006 | Todd et al. | 600/178 |
| 2006/0173259 A1* | 8/2006 | Flaherty et al. | 600/331 |
| 2006/0293563 A1 | 12/2006 | Banik et al. | |
| 2007/0030345 A1* | 2/2007 | Amling et al. | 348/73 |
| 2007/0032697 A1 | 2/2007 | Shimizu et al. | |
| 2007/0066866 A1 | 3/2007 | Noguchi et al. | |
| 2007/0112247 A1 | 5/2007 | Hirata | |
| 2007/0185550 A1 | 8/2007 | Vallapureddy et al. | |
| 2007/0222542 A1* | 9/2007 | Joannopoulos | B60L 11/182 333/219 |
| 2007/0282165 A1 | 12/2007 | Hopkins et al. | |
| 2007/0290814 A1 | 12/2007 | Yoshida | |
| 2008/0177143 A1* | 7/2008 | Yoshida | A61B 1/00016 600/130 |
| 2008/0200758 A1 | 8/2008 | Orbay et al. | |
| 2008/0211634 A1 | 9/2008 | Hopkins et al. | |
| 2008/0246838 A1 | 10/2008 | Chatenever et al. | |
| 2008/0281375 A1* | 11/2008 | Chen | 607/40 |
| 2009/0018395 A1 | 1/2009 | Honda | |
| 2009/0093676 A1 | 4/2009 | Davidson | |
| 2009/0264702 A1 | 10/2009 | Yoshizawa | |
| 2009/0292168 A1 | 11/2009 | Farr | |
| 2010/0023093 A1 | 1/2010 | Govari et al. | |
| 2011/0112602 A1* | 5/2011 | Lee et al. | 607/45 |
| 2011/0193948 A1 | 8/2011 | Amling et al. | |

FOREIGN PATENT DOCUMENTS

| | | | | |
|---|---|---|---|---|
| JP | 2001251611 A | * | 9/2001 | H04N 7/18 |
| JP | 2004113805 A | | 4/2004 | |
| JP | 2005052363 A | | 3/2005 | |
| JP | 2005287150 A | | 10/2005 | |
| JP | 2006061628 A | | 3/2006 | |
| JP | 2007330404 A | | 12/2007 | |
| JP | 2008011609 A | | 1/2008 | |
| JP | 2009261462 A | | 11/2009 | |
| WO | 2006103778 A1 | | 10/2006 | |
| WO | 2007008646 A2 | | 1/2007 | |
| WO | 2007111309 A1 | | 10/2007 | |

OTHER PUBLICATIONS

Center for Materials Science and Engineering and Research Laboratory of Electronics, Massachusetts Institute of Technology; &, Annals of Physics, vol. 323, No. 1, pp. 34-48; Karalis, Aristeidis: "Efficient wireless non-radiative midrange energy transfer" submitted Nov. 7, 2006, 19 pages.

MIT News; Hadley, Franklin; "Goodbye Wires . . . " Jun. 7, 2007; 3 pages.

International Search Report and Written Opinion of the International Searching Authority; PCT/US09/02518; Jun. 4, 2009; 10 pages.

Science Daily; "MIT Demonstrates Wireless Power Transfer"; Jun. 8, 2007; 3 pages.

RF Aystem Lab.—"The Next Generation Capsule Endoscope Sayaka" announced to the market in Dec. 2001, http://www.rfamerica.com/sayaka/index.html. retrieved from Internet on Mar. 20, 2009, 6 pages.

From Wikipedia, the free encyclopedia; "Wireless Energy Transfer"; http://en.wikipedia.org/wiki/Wireless_energy_transfer; retrieved from the Internet on Apr. 17, 2009; 12 pages.

* cited by examiner

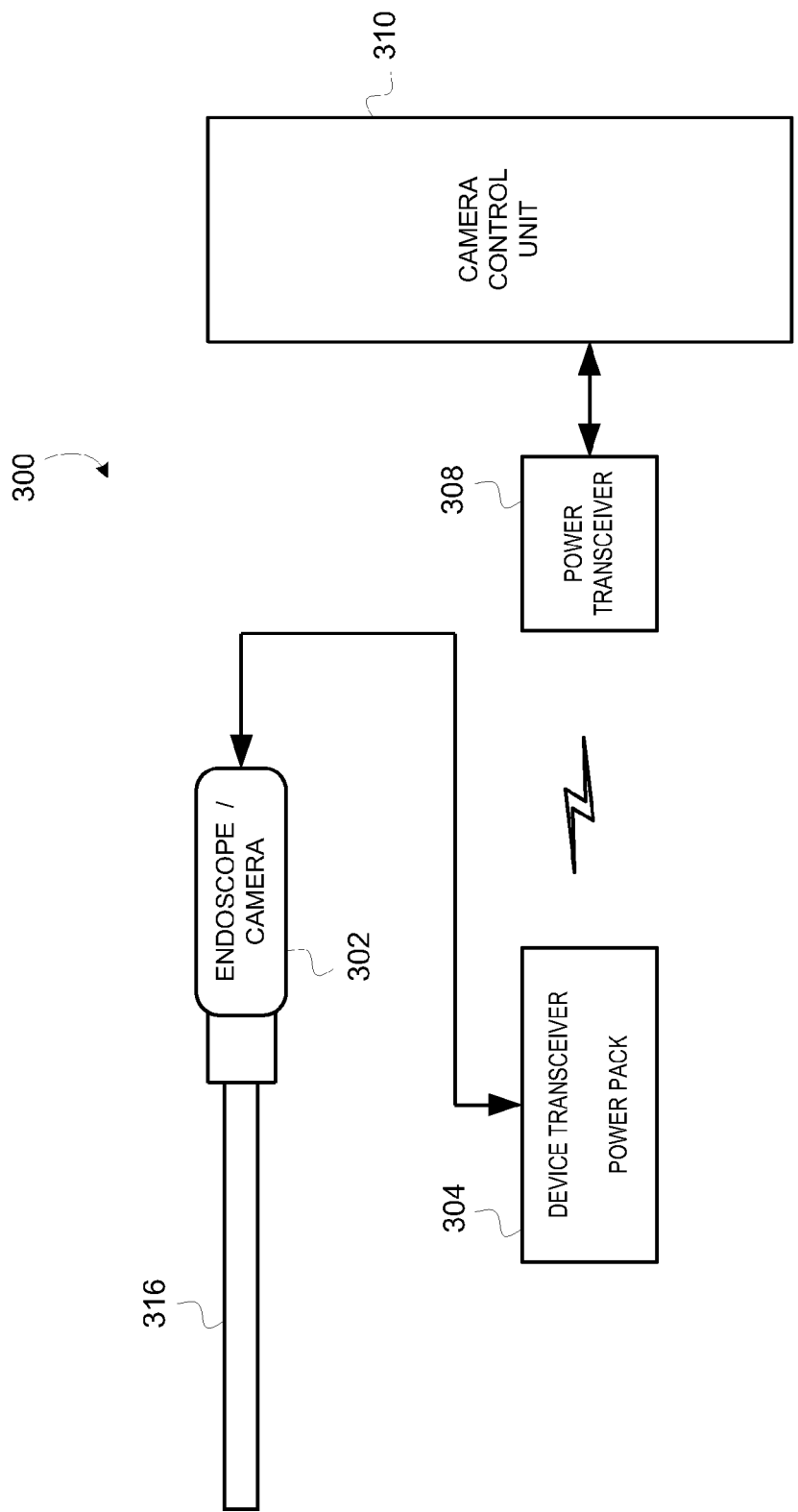

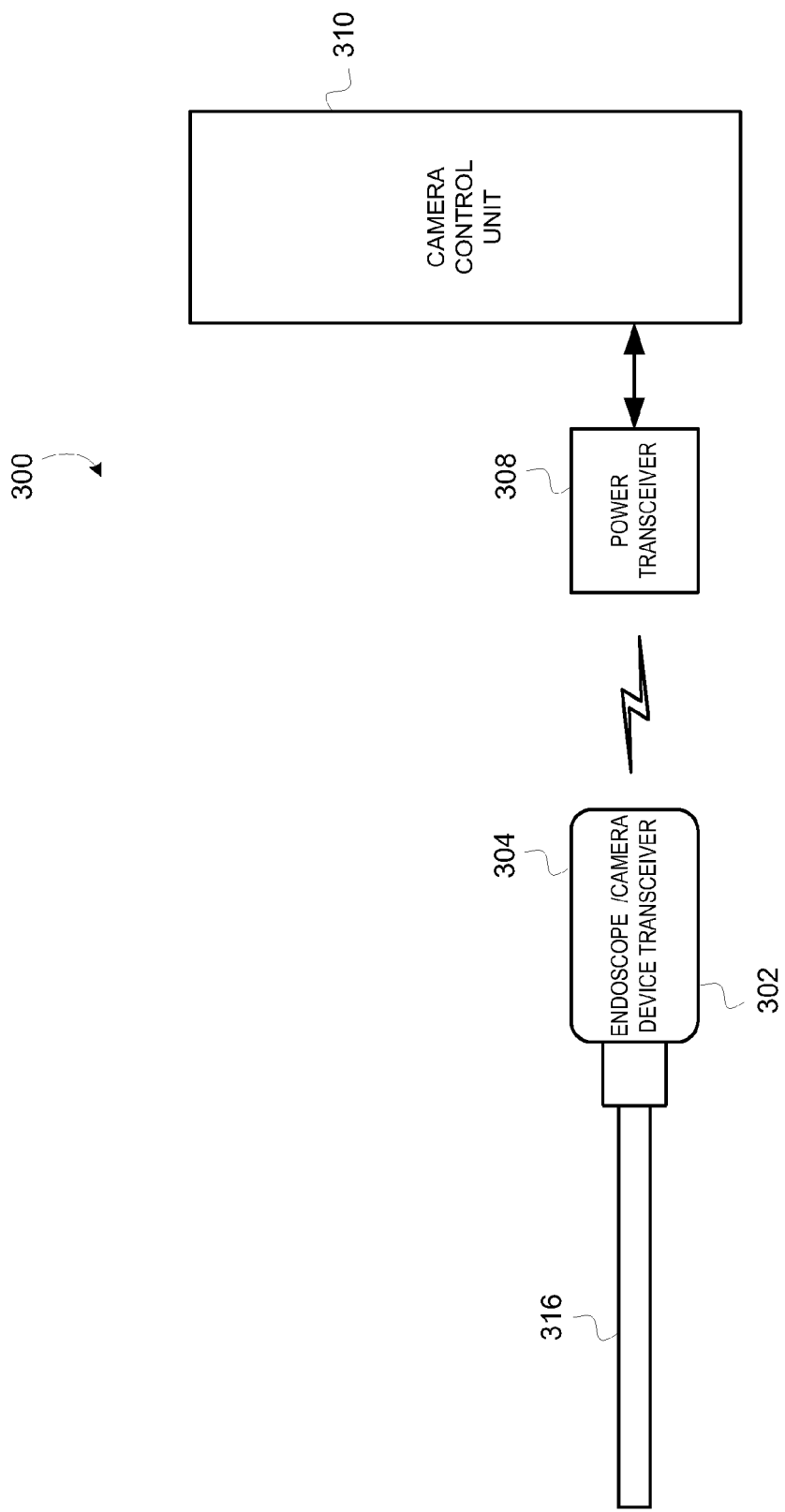

WIRELESSLY POWERED MEDICAL DEVICES AND INSTRUMENTS

CROSS-REFERENCE TO RELATED APPLICATIONS

This application is a continuation-in-part of U.S. patent application Ser. No. 12/425,869 filed Apr. 17, 2009, which claims the benefit of the filing date of U.S. Provisional Patent Application No. 61/047,967 filed Apr. 25, 2008.

FIELD OF THE INVENTION

The invention relates to a wireless medical instrument and more specifically to a medical video instrument that wirelessly receives electrical power for operation of the video instrument providing electrical isolation between the patient and the source of electrical power.

BACKGROUND OF THE INVENTION

Powered medical devices and/or instruments have been in use for many years. However, one of the major drawbacks of such instruments is the relatively large amount of cables required for operation. For example, cutting devices require the use of a power cable to provide electrical power for the medical instrument. Likewise, video endoscopes have traditionally required the use of a power cable and a data transmission line as well as a fiber optic cable for transmission of illuminating light.

These lines are cumbersome and may even present operational difficulties for the user. For example, these cables can get in the way of other surgical instruments and also make the endoscope top heavy and difficult to maneuver. Additionally, surgeons often complain of fatigue because they are constantly working against the weight of the cables attached to their instruments.

Still another problem that cables present is that they can compromise the procedure if mismanaged as contact with the cables, by another individual or with an object, may suddenly cause tugging on an instrument and/or accidentally cause the instrument to be thrust into or impinge upon delicate tissue. In fact, this problem is so prevalent that many surgeons wrap the cables around their wrists several times to prevent cable forces from transferring directly to their instruments.

Yet another problem faced by current system is the lack of electrical isolation between the patient and the source of electrical power. As medical devices are inserted into a patient's body during a procedure, the patient is a risk of receiving an electrical shock if the device ground faults or shorts. Accordingly, a system that will provide for complete electrical isolation between a patient and the source of electrical power would be advantageous.

In an attempt to address some of the problems associated with "wired" devices, a number of systems have sought to provide "wireless" systems with limited success. For example, systems have provided for wireless transmission of image data from an endoscope to a display and have further provided an energy source positioned on the endoscope. This provides the advantage that the cables are eliminated as the power source on the endoscope powers both the image circuitry and a light source (typically an LED) positioned on the endoscope. However, these systems suffer from a number of drawbacks.

First, battery systems continue to be inherently large, heavy and costly. As was previously stated, physicians that have to manipulate a relatively heavy device or fight against relatively heavy cables, suffer from fatigue, especially in relatively complicated and long surgical procedures.

Another problem with battery-powered systems is that they may not be recharged or they may only be partially recharged, thus causing them to shut down or at the very least, causing the device to function at a non-optimal level (i.e. low voltage level) for a portion of the procedure. While procedures may be put into place to limit mistakes in the recharging process, human-error will result in some devices not being charged or not being fully recharged. It is widely know that it is critical to limit the time that a patient is under general anesthesia. Any delay due to, for example, failure of a medical instrument or even sub-standard operation and delay as a new instrument is obtained, connected and powered up should therefore be avoided if at all possible.

Still another problem with battery-powered systems is that batteries inherently deteriorate over time. For example, initially a battery may provide a sufficient amount of power output to operate a particular medical instrument for a given period. However, as the battery is used and recharged again and again, that power output slowly decreases until the battery can no longer maintain sufficient charge to operate the medical device for the length of the procedure. While the battery may function sufficiently for a certain number of operations, it is unclear if and/or when the battery will fail, for example, during a medical procedure. Regular replacement of batteries can limit this problem, however, this greatly increases the cost associated with using wireless devices. Battery testing can also limit this problem, but this takes time and involves human error if the individual forgets, makes a mistake in testing or misreads the results.

In still another system disclosed in U.S. Patent Application Publication No. 2007/0290814 (Yoshida), a wireless power feeding system is provided for wirelessly transmitting electrical energy to a capsule endoscope system. The system in Yoshida includes an image pickup unit that is swallowed by the individual (i.e. a capsule) and generates and transmits an image signal of the area adjacent to the capsule. The Yoshida system is a capsule that will slowly work its way through the body providing various still frame images of the areas (e.g. gastro-intestinal tract) through which it passes. Yoshida uses an inductive power transfer method that is based on the orientation of the power transmitting coil relative to the power receiving coil. For example, Yoshida states that "the amount of power received by a power receiving coil is maximized when the winding axis of a power transmitting coil substantially matches the winding of the power receiving coil" and that "direction and position of the magnetic member" is "changed to collect more of the magnetic flux." (Pars. 55-57) Accordingly, the position and orientation of the transmitter and receiver is important to Yoshida to ensure a sufficient amount of energy is transmitted to the capsule. Such a system may be acceptable for use with, for example, a capsule that is not manipulated by a surgeon. However, in an active medical procedure, the surgeon is regularly (if not almost continually) manipulating medical instruments (e.g. cutting tools, video endoscopes, etc.) as necessary to accomplish the procedure. Therefore, the system taught in Yoshida could not be used for an active medical procedure as the power transmitting coil would not regularly be aligned with the receiving coil. It would be virtually impossible for the surgeon to perform the procedure if the surgeon had to maintain the tool in alignment with the power transmitter as the surgeon needs to freely move the tool without regard to external issues. In any event, the capsule system is certainly not designed for manipulation by the physician (i.e. it is designed to be ingested by the patient).

Another limitation of the system taught in Yoshida, is that it is not provided to transmit a video stream of information that requires 30-60 frames of information per second. Rather, the system taught in Yoshida is a passive system that provides still frame images as it passes through the body. (Pars. 24-25) In fact, in view of the limited amount of power that can be transmitted to the capsule, it is questionable whether the video could provide a video stream of the area it is slowly passing through. Additionally, the system taught in Yoshida does not provide for the constant light output needed for continual illumination for video transmission. The power requirement to perform this functionality is orders of magnitude higher than is contemplated in the Yoshida system.

SUMMARY OF THE INVENTION

What is desired therefore is a system and method that eliminates the problem associated with "wired" medical devices and further addresses the problems associated with battery-powered medical devices.

It is also desired to provide a system and method that reduces the weight of a medical instrument.

It is further desired to provide a system and method that eliminates the electrical cables connected to a medical instrument such that the physician is unimpeded to perform a medical procedure.

It is still further desired to provide a wirelessly powered transmission system for a medical instrument that allows for the transmission of streaming video.

It is yet further desired to provide a system and method that provides a highly reliable wirelessly powered transmission system for a medical instrument with reduced operational costs.

These and other objectives are achieved in one advantageous embodiment by the provision of a medical instrument that provides for the wireless transmission of power to operate the instrument. While wireless transmission of data has been facilitated, the provision of power has been provided either by means of electrical cables or by a portable power source (e.g. a battery positioned on the medical instrument itself). The present invention seeks to provide electrical power to the medical instrument via a wireless coupling.

It is contemplated that in one embodiment, the medical instrument can draw enough power via a resonate coupling arrangement, to function without need of any type of electrical storage device positioned on the medical instrument. In another embodiment, a reduced weight electrical storage device may by positioned on the medical device to store a very limited amount of electrical power in the event of a momentary disconnection from the wireless power coupling. In the second embodiment, the medical device would automatically start recharging when it enters the vicinity of a wireless power sending unit.

It is contemplated that the medical instrument can comprise virtually any type of powered medical instrument, including for example, a cutting/cauterizing tool, an irrigation/aspiration tool, a visualization tool, a recording and/or printing device, etc. In the case of a video endoscope, it is contemplated that in addition to wireless coupling to a power sending device, the endoscope will wirelessly couple to a control unit, in which wirelessly transmitted data would be transmitted between the endoscope and the control unit including but not limited to, control data, command data, identification data, maintenance data, image data and combinations thereof. For example, once the endoscope is brought in the vicinity of a wireless power sending unit, the endoscope may power up and communicate with a control unit identifying the type of endoscope such that the control unit adjusts its setting to proper control the particular endoscope.

It is still further contemplated that the medical device may be coupled to a network. In this example, the medical instrument can be seamlessly integrated into a surgical station that may include various differing types of medical instruments that are integrated into a single surgical station. In the event the medical device comprises an endoscope, the image data may be transmitted over the network connection for viewing by other individuals, for example, for teaching or instruction. The image stream may further be recorded for later consultation. In any event, the medical instrument will be provided with a wireless power source such that the physician is provided with a reliable, light-weight, cost-effective device that will not present the interference issues of "wired" medical devices.

The system may further be utilized with known endoscopes that include a camera head in the endoscope and an optical connection port. For example, the endoscope may be provided with an endoscope transceiver that may be plugged into or affixed to the endoscope and the camera control unit (CCU) may be provided with a corresponding CCU transceiver that may be coupled to the CCU. In this manner electrical power may be transferred from the CCU transceiver to the endoscope transceiver for powering the endoscope and image data and signals may be wirelessly transmitted between the endoscope and the CCU. It is contemplated that a standard optical cable may extend between the endoscope and a light source or the light source may be provided in the endoscope and powered by the wirelessly sent electrical power.

For this application the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network or inter-network.

The terms "first" and "second" are used to distinguish one element, set, data, object or thing from another, and are not used to designate relative position or arrangement in time.

The terms "coupled", "coupled to", and "coupled with" as used herein each mean a relationship between or among two or more devices, apparatus, files, programs, media, components, networks, systems, subsystems, and/or means, constituting any one or more of (a) a connection, whether direct or through one or more other devices, apparatus, files, programs, media, components, networks, systems, subsystems, or means, (b) a communications relationship, whether direct or through one or more other devices, apparatus, files, programs, media, components, networks, systems, subsystems, or means, and/or (c) a functional relationship in which the operation of any one or more devices, apparatus, files, programs, media, components, networks, systems, subsystems, or means depends, in whole or in part, on the operation of any one or more others thereof.

The term "surgical suite" as used herein means an integrated surgical system that includes one or more controllers; a bus; one or more medical devices (e.g. cutting/cauterizing tool(s), irrigation tool(s), aspiration tool(s), visualization tool(s), recording and/or printing devices, etc.); where the various devices are coupled to the bus and controlled by an interface device.

The term "resonant" interaction as used herein, is used to describe the relatively strong coupling that occurs between two substantially same-frequency objects (e.g. a transmitter/receiver), while interacting relatively weakly with other off-resonant environmental objects. "Resonant" interaction would further encompass resonant evanescent coupling where resonant coupling occurs through the overlap of non-radiative near-fields of two objects.

The terms "process" and "processing" as used herein each mean an action or a series of actions including, for example, but not limited to the continuous or non-continuous, synchronous or asynchronous, direction of data, modification, formatting and/or conversion of data, tagging or annotation of data, measurement, comparison and/or review of data, and may or may not comprise a program.

In one advantageous embodiment a video endoscope system is provided comprising an endoscope which has an imager generating video image data stream, a light source generating illuminating light and an endoscope transceiver coupled to and providing power to the imager and the light source. The video endoscope system further includes a power transceiver generating a resonant magnetic field. The endoscope transceiver is tuned to the resonant magnetic field such that resonant interaction occurs between the endoscope transceiver and the power transceiver and electrical power is transmitted to the endoscope transceiver via the resonant interaction. The system further includes a display coupled to the endoscope. The endoscope system is provided such that the endoscope wirelessly transmits the video image data stream to the display and the image data is presented on the display In another advantageous embodiment a method for displaying a video data image stream on a display is provided comprising the steps of positioning an imager in an endoscope, positioning a light source in the endoscope and positioning an endoscope transceiver in the endoscope. The method also includes the steps of coupling the endoscope transceiver to the imager and the light source and providing a power transceiver. The method may also include the steps of generating a resonant magnetic field with the power transceiver and tuning the endoscope transceiver to the resonant magnetic field such that resonant interaction occurs between the endoscope transceiver and the power transceiver. The method further includes the steps of transmitting power from the power transceiver to the endoscope transceiver via the resonant interaction and powering the imager and the light source with the power received by the endoscope transceiver. It is contemplated that the method also includes the steps of generating illuminating light with the light source and generating a video image data stream with the imager. Finally, the method includes the steps of wirelessly transmitting the video image data stream from the endoscope to a display and displaying the video image data stream on a display.

In still another advantageous embodiment a medical device system is provided comprising a medical device that has an electronic circuit and a resonant receiver coupled to and providing electrical power to the electrical circuit. The medical device system further includes a power transmitting unit including a resonant transmitter generating a resonant magnetic field. The medical device system is further provided such that the resonant receiver is tuned to the resonant magnetic field where resonant interaction occurs between the resonant receiver and the resonant transmitter and electrical power to operate the medical device is transmitted to the resonant receiver via the resonant interaction.

In yet another advantageous embodiment an endoscope system is provided comprising an endoscope that has a light source generating illuminating light and an endoscope transceiver coupled to and providing power to the light source. The endoscope system further includes a power transceiver generating a resonant magnetic field. The endoscope system is provided such that the endoscope transceiver is tuned to the resonant magnetic field such that resonant interaction occurs between the endoscope transceiver and said power transceiver and power is transmitted to the endoscope transceiver via the resonant interaction.

In still another advantageous embodiment an endoscope system is provided comprising an endoscope and a camera that is coupled to the endoscope, where the camera generates image data. The system further comprises a camera control unit and a device transceiver coupled to the camera. The system still further comprises a light source generating illuminating light and a power transceiver coupled to the camera control unit, where the power transceiver generates a resonant magnetic field. The system is provided such that the device transceiver is tuned to the resonant magnetic field so that resonant interaction occurs between the device transceiver and the power transceiver and power is transmitted to the device transceiver by the resonant interaction wherein electrical power is provided to the camera by the device transceiver.

In yet another advantageous embodiment a method for providing an endoscope system that comprises an endoscope, a camera and a camera control unit is provided where the method comprises the steps of coupling the camera to the endoscope, coupling a device transceiver to the camera/endoscope combination and coupling a power transceiver to the camera control unit. The method also includes the steps of generating a resonant magnetic field with the power transceiver and coupling the device transceiver to the power transceiver, the device transceiver tuned to the resonant magnetic field generated by the power transceiver so that resonant interaction occurs between the device transceiver and the power transceiver. The method may also include the steps of transmitting power to the device transceiver from the power transmitter, generating electrical power with the device transceiver and providing electrical power from the device transceiver to the camera/endoscope combination. The method may further include the steps of generating illuminating light with a light source, transmitting the illuminating light to an area to be viewed and positioning an imaging device on the camera/endoscope. Finally, the method includes the steps of receiving reflected light from the area to be viewed with the imaging device, generating image data with the imaging device and transmitting the image data from the camera to the camera control unit via the device transceiver and power transceiver coupling arrangement.

Other objects of the invention and its particular features and advantages will become more apparent from consideration of the following drawings and accompanying detailed description.

BRIEF DESCRIPTION OF THE DRAWINGS

FIG. 13 is a block diagram according to the advantageous embodiment of 1.

FIG. 14 is a block diagram according to the advantageous embodiment of 1.

DETAILED DESCRIPTION OF THE INVENTION

Figure 1:
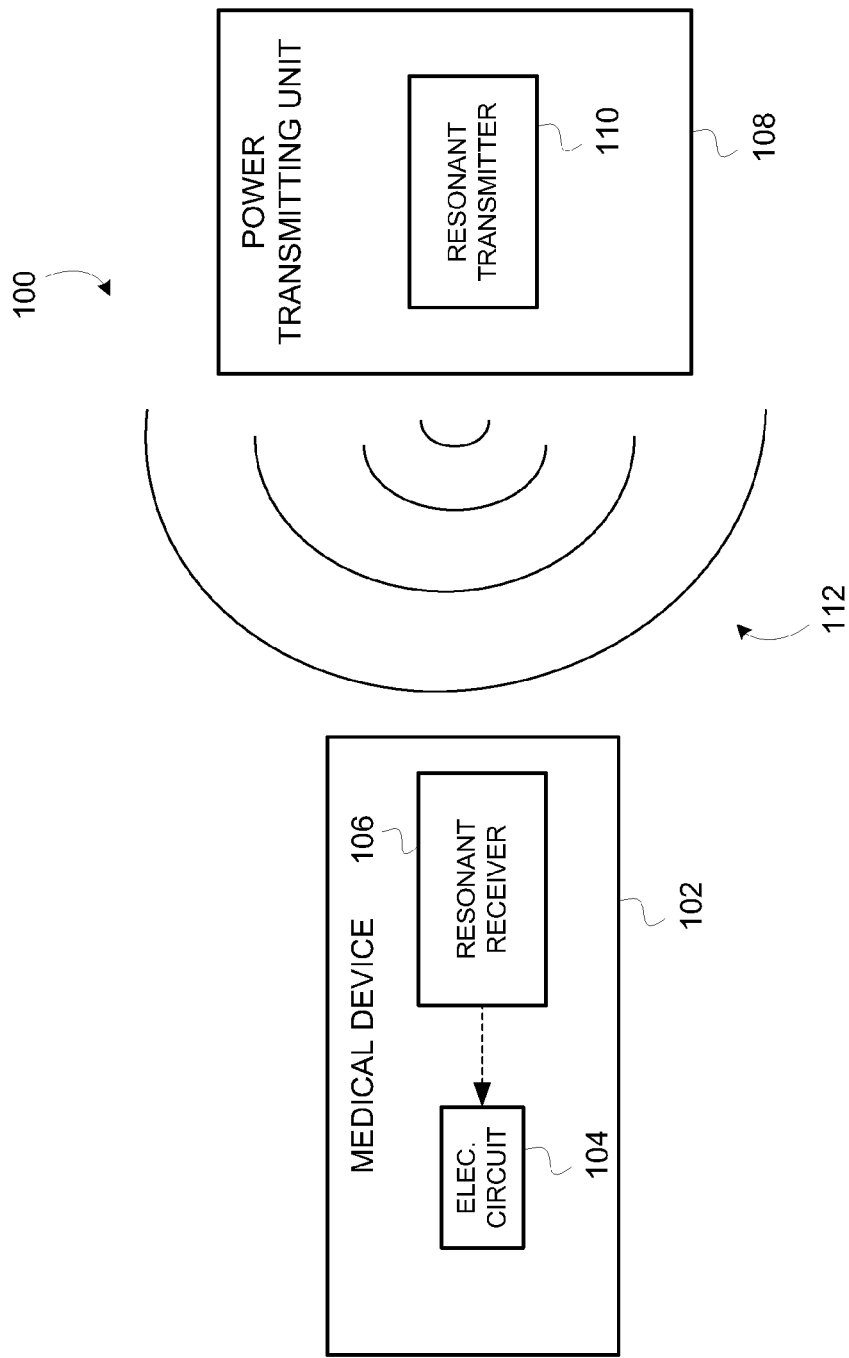
FIG. 1 is a block diagram of an advantageous embodiment of the present invention.

Referring now to the drawings, wherein like reference numerals designate corresponding structure throughout the views.

FIG. 1 generally depicts system 100 for providing electrical power to a medical device 102. It is contemplated that medical device 102 could comprise virtually any type of powered medical device, including but not limited to, a cutting/cauterizing tool, an irrigation/aspiration tool, a visualization tool, a recording and/or printing device and the like. Medical device 102 is provided with electronic circuit 104 and resonant receiver 106. Electronic circuit 104 may comprise any electronic/electrical circuit(s) used to operate medical device 102. Electronic circuit 104 is electrically coupled to resonant receiver 106.

Also provided in FIG. 1 is power transmitting unit 108 that includes resonant transmitter 110. It is contemplated that resonant transmitter 110 generates a resonant magnetic field 112 (depicted by the concentric lines) that transmits from power transmitting unit 108. Resonant receiver 106 is "tuned" to the same frequency as resonant magnetic field 112 such that, when resonant receiver 106 is moved to a location within resonant magnetic field 112, a strong resonant coupling occurs between resonant receiver 106 and resonant transmitter 110. The resonant coupling in one advantageous embodiment, comprises evanescent stationary near-field. While the transmitter/receiver may comprise virtually any type of resonant structure, it is contemplated that in an advantageous embodiment, the electromagnetic resonant system may comprise dielectric disks and capacitively-loaded conducting-wire loops. This arrangement provides the advantages of a strong coupling for relatively large and efficient power transfer as well as relatively weak interaction with other off-resonant environmental objects in the vicinity.

Figure 2:
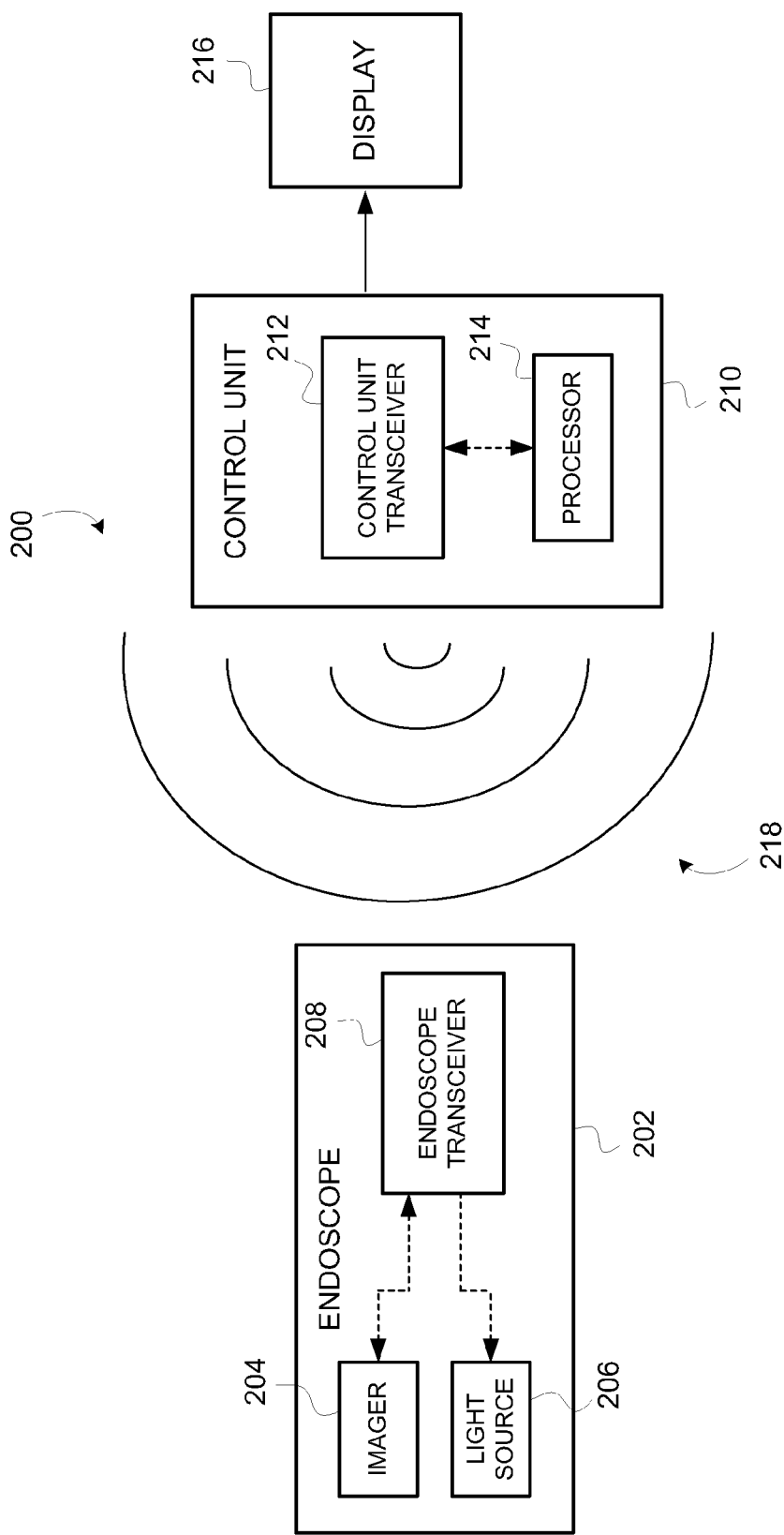
FIG. 2 is a block diagram according to the advantageous embodiment of FIG. 1.

Turning now to FIG. 2, system 200 generally includes an endoscope 202 having an imager 204, a light source 206 and an endoscope transceiver 208. System 200 further includes control unit 210 having control unit transceiver 212 and processor 214. Display 216 is shown coupled to control unit 210.

It should be noted that control unit transceiver 212 generates a resonant magnetic field 218 similar to that described in connection with FIG. 1 and will not be re-described here.

Endoscope transceiver 208 receives electrical power via resonant magnetic field 218, which is transmitted to imager 204 and light source 206 for operating the respective devices. It is contemplated that imager 204 may comprise virtually any type of imaging device, including for example, a CCD or CMOS device for generating image data. Likewise, light source 206 may comprise virtually any type of device for providing illuminating light, such as, for example, an LED. It is further noted that the endoscope comprises a shaft (not illustrated), either rigid or flexible, that is inserted into a body cavity on which a medical procedure is to be performed. In one embodiment, the light source is located in a handle portion of the endoscope and illuminating light is transmitted down a light path to a distal end of the shaft to illuminate an area ahead of the shaft. The image may be positioned at the distal end of the shaft to receive or pick up reflected light to generate image data. The image data may then be wirelessly transmitted to the control unit.

It should be noted that the image data is provided as a video image data stream comprising from about 30 to about 60 frames of data per second. This is possible as the resonant coupling allows for sufficient electrical power to be transmitted to the endoscope transceiver 208.

The processor 214 is positioned in control unit 210 and is designed to receive and process the received image data. It is contemplated that the processor 214 may further comprise a configurable unit to process the image data in the format received from the imager 204.

Once the image data is processed into a format compatible for use with display 216, the image data is transmitted to and displayed on display 216 for observation by a user/viewer.

It is contemplated that endoscope transceiver 208 and control unit transceiver 212 are provided to resonantly couple electrical power from control unit 210 to endoscope 202 for operation of the electronics in endoscope 202. It is further contemplated that endoscope transceiver is adapted to transmit the image data generated by imager 204 to control unit transceiver 212 for processing by processor 214. In one advantageous embodiment, the transmission of image data occurs via RF transmission. In another advantageous embodiment, the transmission of image data occurs via the resonant coupling method previously described. In either event, there is two-way transmission (i.e. electrical power to endoscope 202 and image data to control unit 210).

Figure 2A:
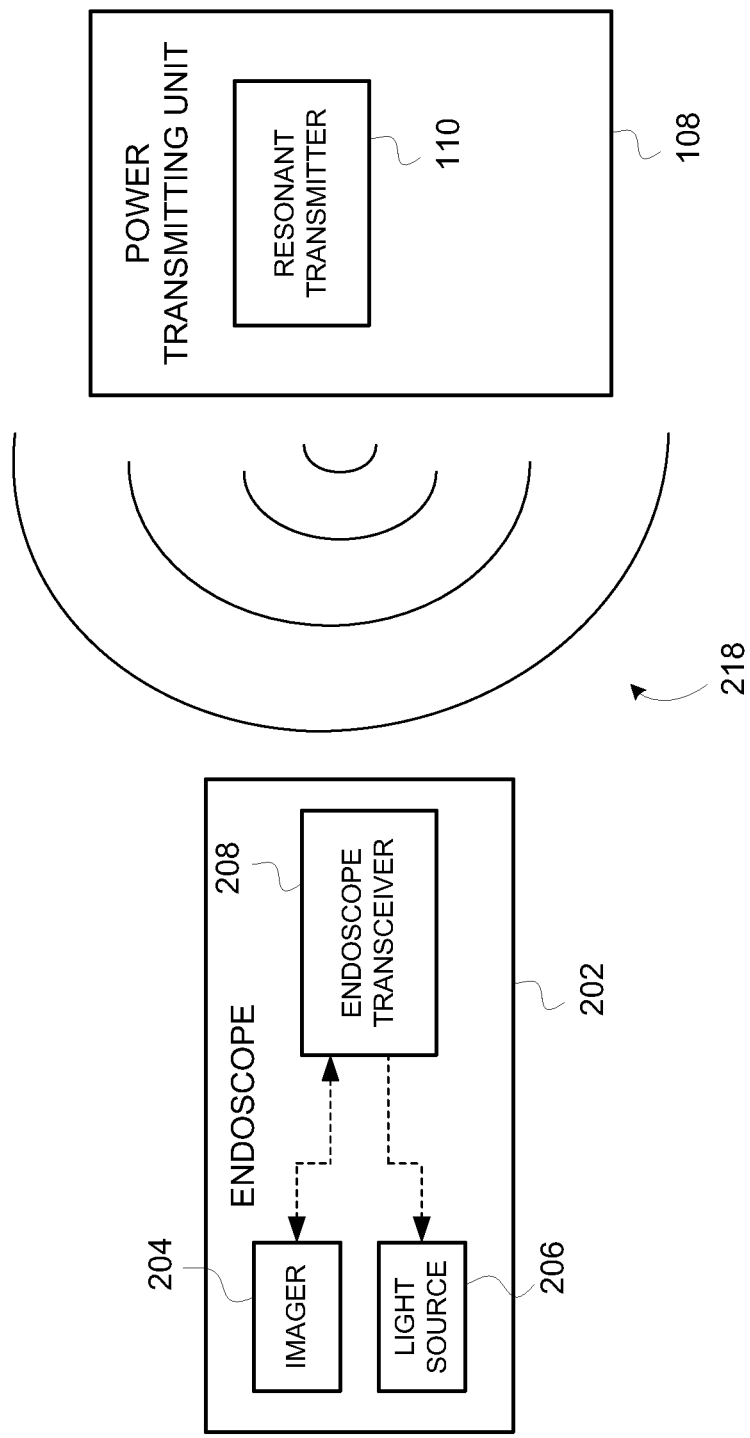
FIG. 2A is a block diagram according to the advantageous embodiment of FIG. 1.

FIG. 2A illustrated another embodiment of the present invention highlighting that the power transmitting unit 108 including the resonant transmitter 110 discussed in connection with FIG. 1 need not be located in a control unit, but may in fact, merely be positioned in the vicinity of the endoscope 202.

Figure 3:
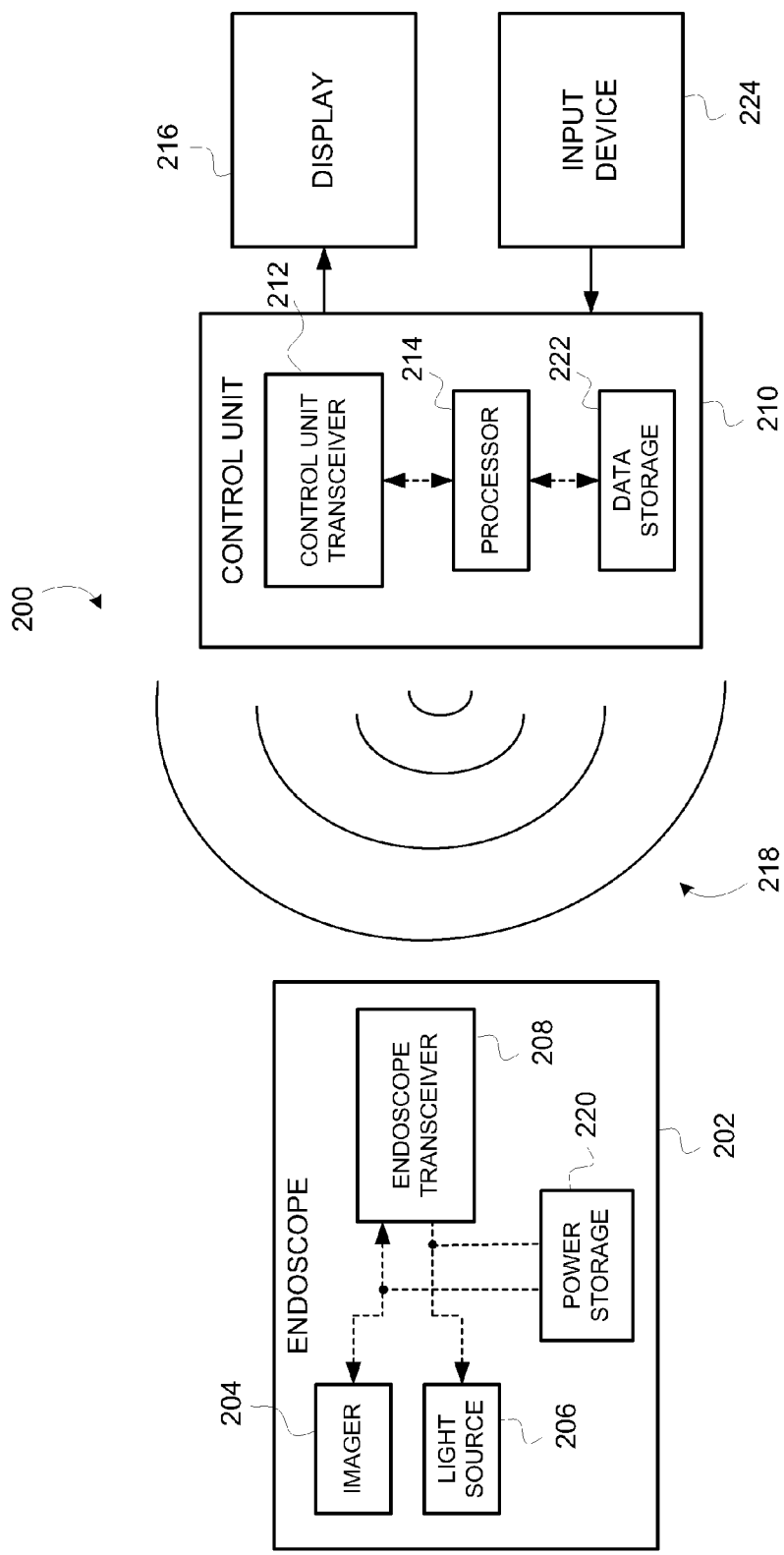
FIG. 3 is a block diagram according to the advantageous embodiment of FIG. 2.

Referring now to FIG. 3, system 200 is depicted including the endoscope 202 and control unit 210 as per FIG. 2. The function and operation of the various features listed in FIG. 2 are substantially identical and will not be re-described in connection with FIG. 3.

Also included in endoscope 202 is power storage device 220, which may comprise, for example, a rechargeable battery. It is contemplated that battery 220 may comprise virtually any type of rechargeable battery as is known in industry. However, power storage device 220 will advantageously be kept relative small and light-weight to keep the weight of endoscope 202 to a minimum.

As can be seen in FIG. 3, power storage device 220 is coupled to the electrical connections between imager 204 and light source 206 and endoscope transceiver 208, such that, in the event that the resonant coupling between endoscope transceiver 208 and control unit transceiver 212 is lost, power storage device 220 will provide electrical power to both imager 204 and light source 206. It is still further contemplated that when endoscope transceiver is resonantly coupled to control unit transceiver 212, power storage device 220 will automatically charge. While an on-board power source is provided in endoscope 202 in this particular embodiment, it should be noted that the power storage device 220 may be provided relative small in size and weight. Accordingly, due to the relatively small and light-weight characteristics of storage device 220, the endoscope is not designed to indefinitely run on of the power storage device 220.

Also illustrated in FIG. 3 is data storage 222, which is coupled to processor 214. While data storage device is illustrated as residing in control unit 210, it is contemplated that data storage device may reside anywhere and may include virtually any type of data storage device including, for example, a hard drive device, RAM, ROM, optical storage, a USB thumb drive or the like, which is connected locally or via a network connection (including e.g., the Internet).

Input device 224 is also shown coupled to control unit 210. Control unit 224 may comprise virtually any type of interface for a user to input commands. For example, input device 224 may comprise a keyboard, a control panel, voice activation, a USB device, etc. Additionally, while display 216 and input device 224 are illustrated as different devices, it is contemplated that display 216 may comprise a touch screen such that input device and display 216 are embodied in a single device.

Accordingly, by means of the input device 224, a user may save the image data to data storage 222. In another advantageous embodiment, a user is able to access the saved image data to be replayed on display 216. It is contemplated that, for example, the image data that is being displayed on the display during a procedure could be paused, re-wound and re-played for the physician. It is still further contemplated that the image data could be annotated by the physician, including for example, a written annotation attached to the file or even an audio or visual annotation to the image data.

Figure 4:
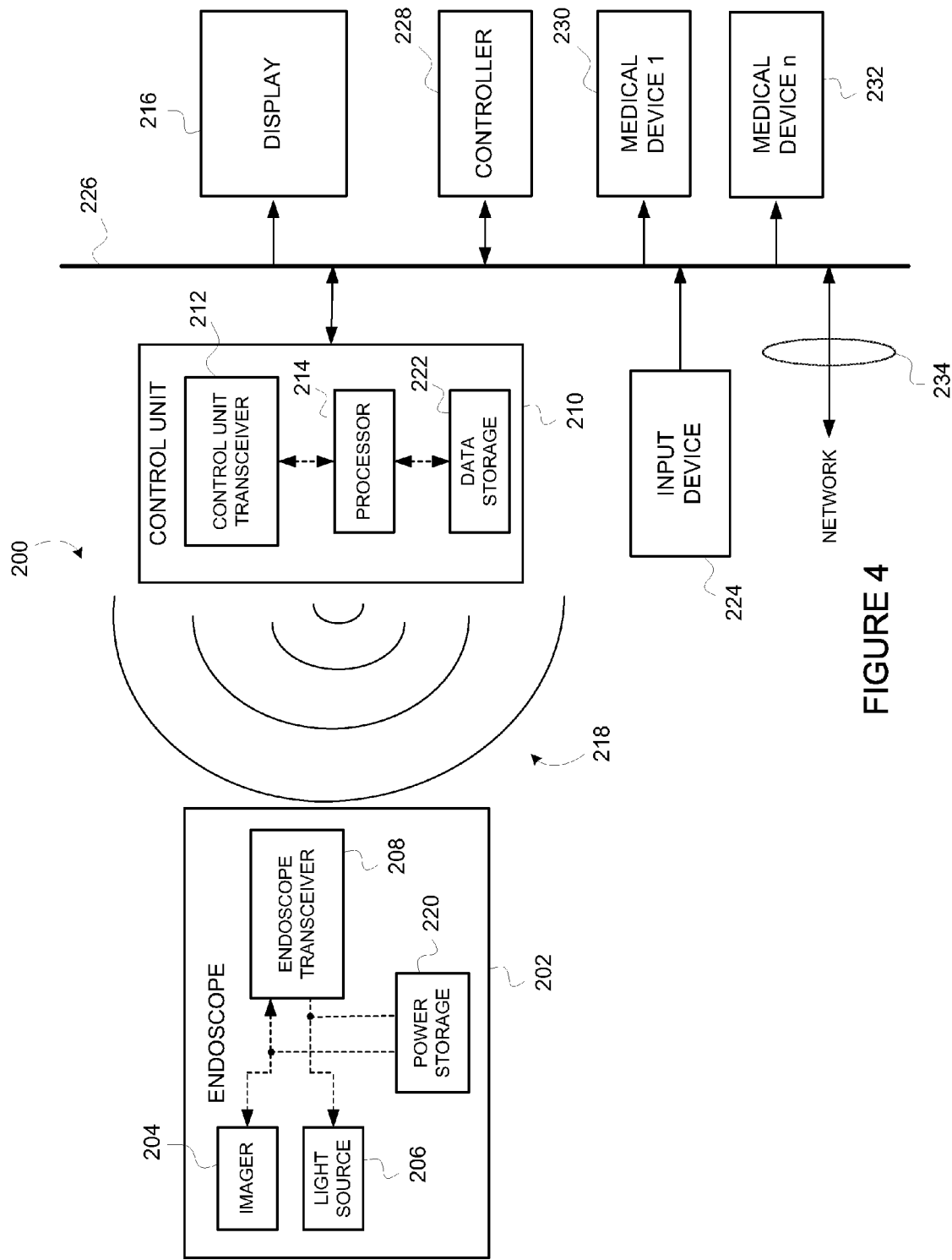
FIG. 4 is a block diagram according to the advantageous embodiment of FIG. 2.

Referring now to FIG. 4, the system 200 further includes a connection to a bus 226 to which are connected a controller 228 and various medical devices (230, 232). It is further contemplated that a network connection 234 may be provided such that the system 200 may be accessed via the Internet.

The configuration illustrated in FIG. 4 is one configuration that is generally known as a "surgical suite." It is contemplated that the medical devices (230, 232) may comprise virtually any type of medical device that may be operated by input device 224 and controller 228 including, but not limited to, cutting/cauterizing tool(s), irrigation tool(s), aspiration tool(s), visualization tool(s), recording and/or printing devices, etc. It is further contemplated that the surgical suite may be a rack mounted arrangement that may be portable from one surgical room to the next.

Figure 5:
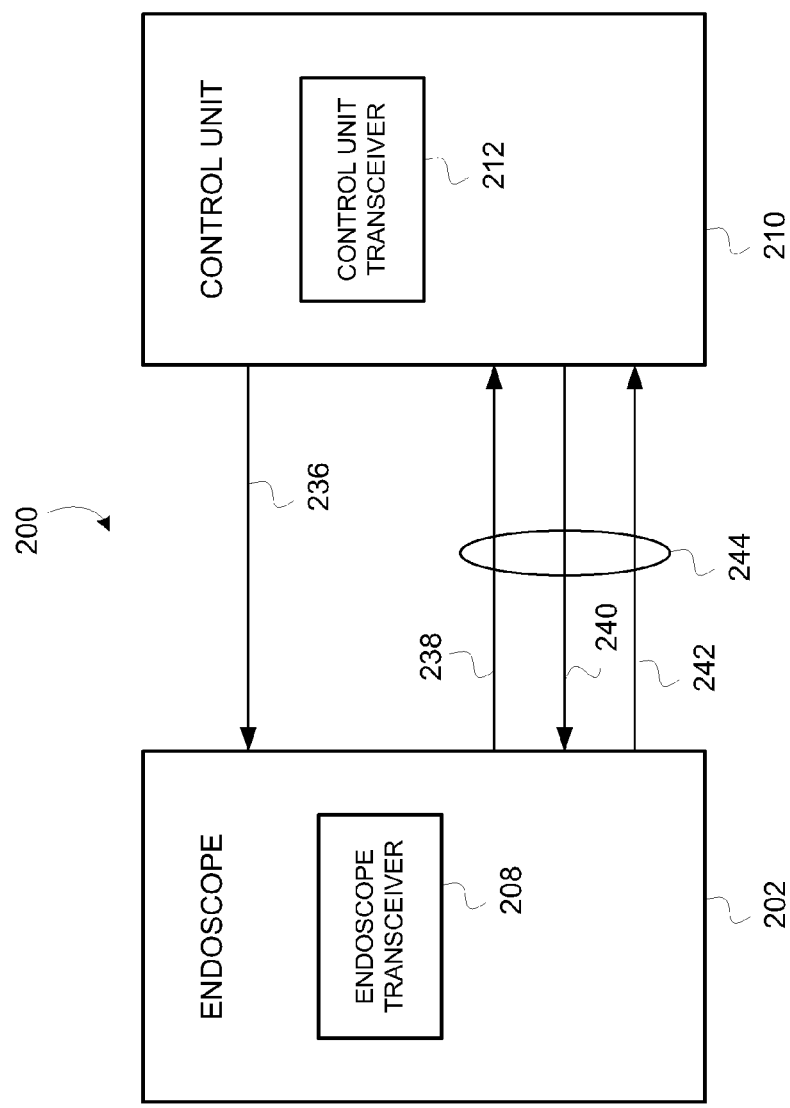
FIG. 5 is a block diagram according to the advantageous embodiment of FIG. 2.

FIG. 5 is provided to illustrate some of the communications that occur between endoscope 202 and control unit 210. For example, when endoscope 202 is brought within the resonant magnetic field emanating from control unit 210, resonant coupling occurs between the endoscope transceiver 208 and control unit transceiver 212 such that electrical power is transmitted 236 to endoscope 202.

Once endoscope 202 is powered up, information is transmitted over a data channel 244 identification data is transmitted to control unit 210 that identifies the type and settings of endoscope 202. Control unit 210 then adjusts its internal settings so as to be able to properly receive the image data from endoscope 202. Once configured, control unit 210 may then send command/control data 240 to endoscope for operating endoscope 202. Endoscope 202 will then begin transmitting a video image data stream 242 to control unit 210 for processing and display.

Figure 6:
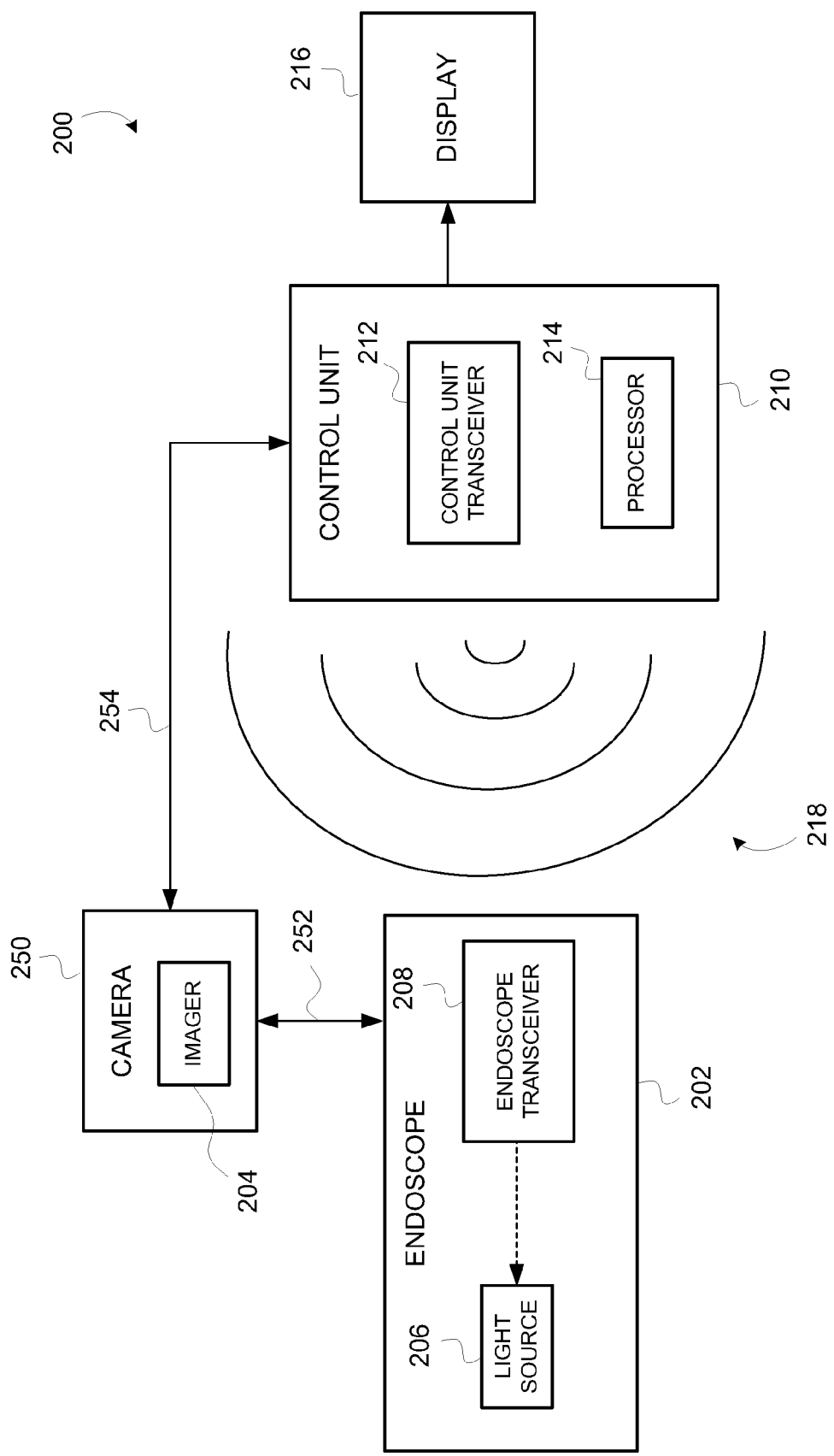
FIG. 6 is a block diagram according to the advantageous embodiment of 1.

FIG. 6 is still another embodiment of the present invention similar to that described in connection with FIG. 2, however, also included are camera 250, coupling 252 and coupling 254.

The embodiment if FIG. 6 is designed for an endoscope 202 with a detachable camera 250, where the camera may already have an independent connection (coupling 254) to the control unit 210. Coupling 254 may comprise a hard-wired connection or a wireless connection for the transmission of both power and/or data. This could allow for the use of existing cameras with endoscope having the transceiver arrangement where only the endoscope receives power via resonant magnetic field 218.

Likewise, coupling 252 may comprise a connection that allows for the transmission of reflected light received by the endoscope to be transmitted to the camera 250. Alternatively, it is contemplated that the imager 204 may be positioned in the endoscope and the camera 250 receives a data stream via coupling 252.

Many differing configurations for the transmission and reception of signals can be envisioned in this system. For example, it is contemplated that power may be transmitted to both the endoscope and camera via resonant magnetic field 218 while data may be transmitted between camera 250 and control unit 210 via coupling 254. The data transmitted via coupling 254 may include, for example, the video data stream, control and command data. Alternatively, the video data stream the video data stream is wirelessly transmitted on a data channel via resonant magnetic field 218 while that control and command data are transmitted between camera 250 and control unit 210 via coupling 254 and vice versa.

Alternatively, the endoscope may be provided as a direct visualization endoscope where camera or video functionality may or may not be provided.

Figure 7:
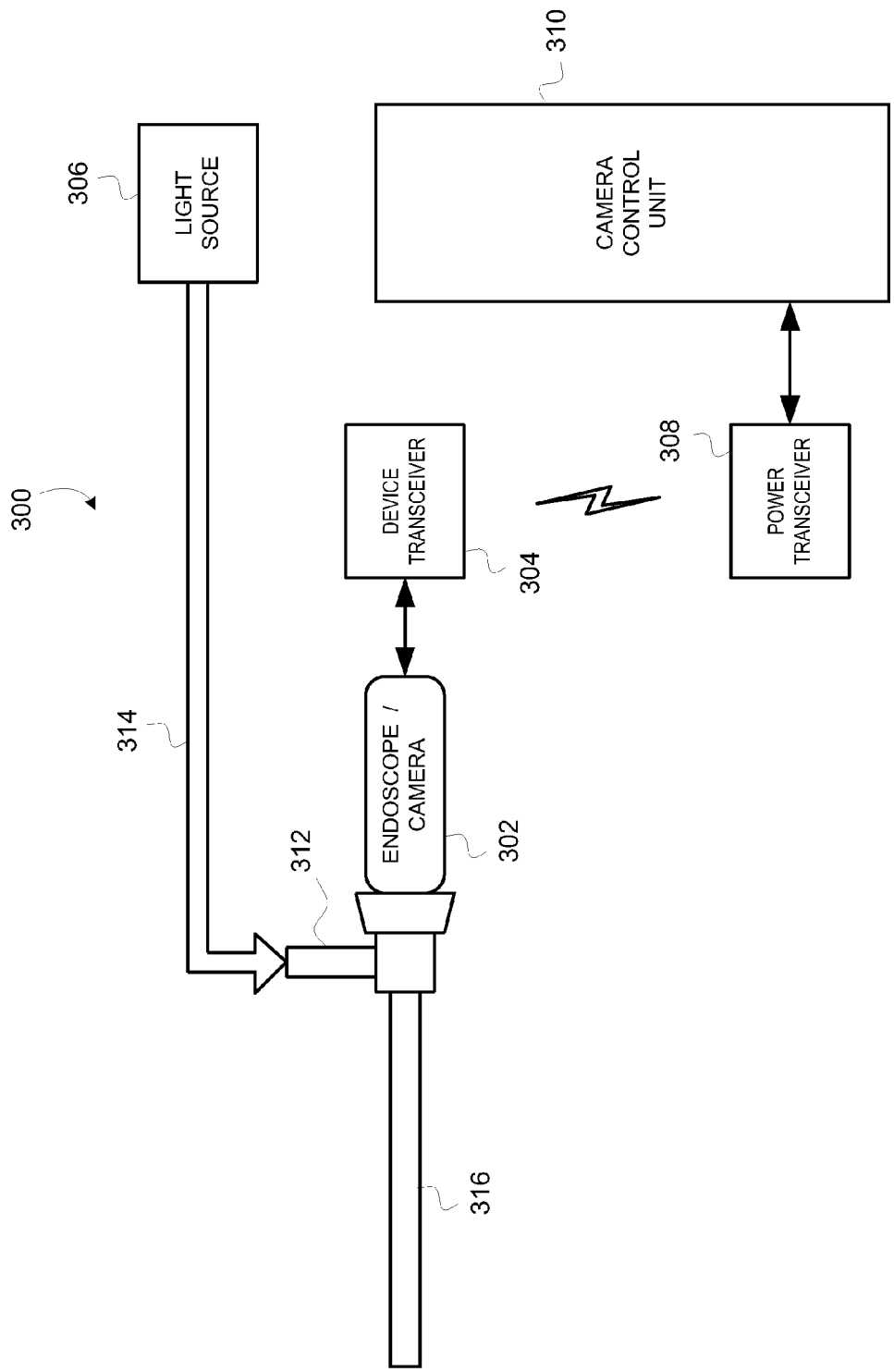
FIG. 7 is a block diagram according to the advantageous embodiment of 1.
Figure 7A:
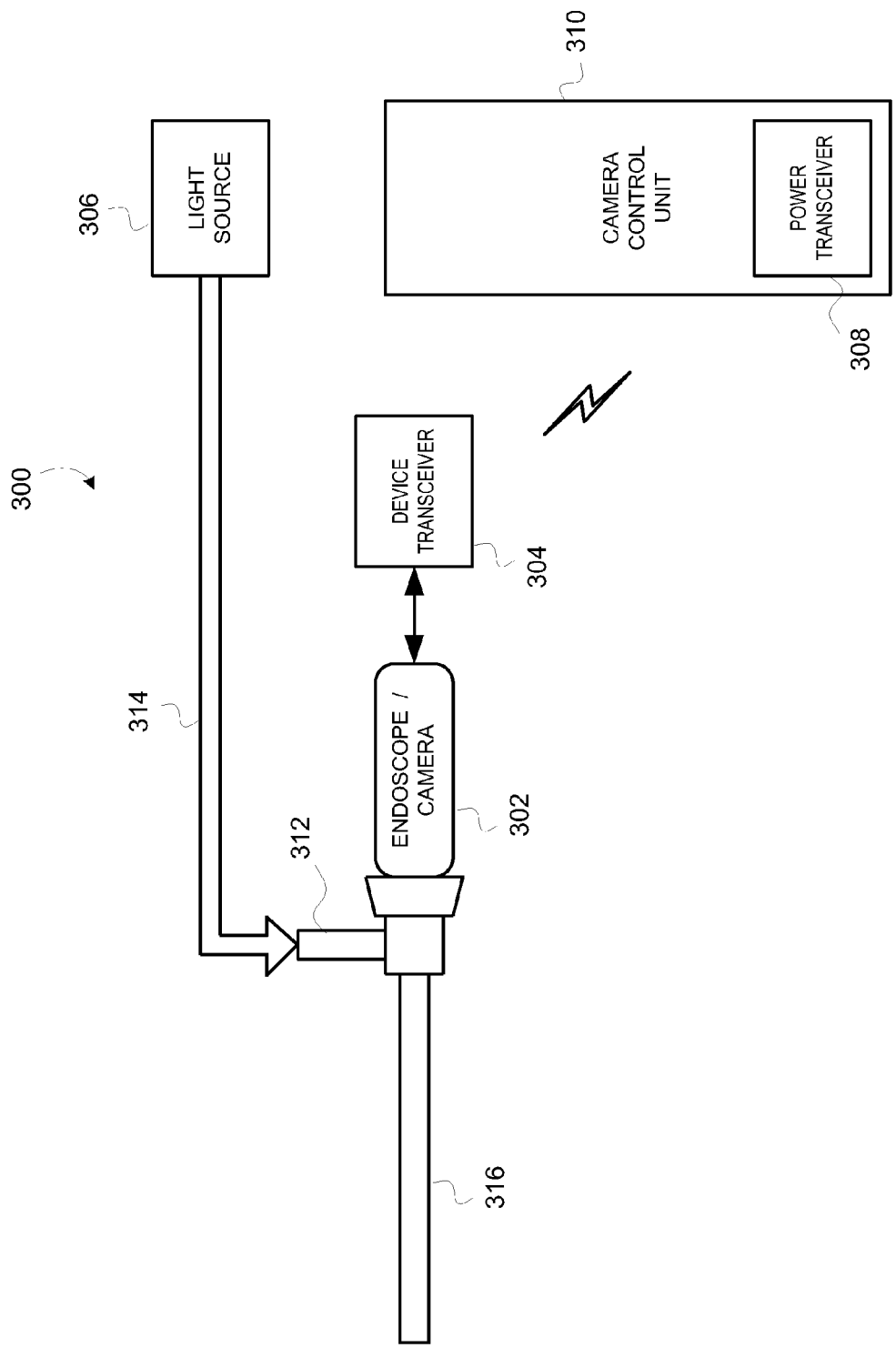
FIG. 7A is a block diagram according to the advantageous embodiment of 7.

FIGS. 7-14A illustrate various embodiments of endoscope system 300 according to the invention. For example, FIGS. 7 and 7A illustrate an embodiment that includes an endoscope/camera 302 that is coupled to a device transceiver 304. Device transceiver 304 is coupled to power transceiver 308 via a wireless resonant coupling as previously discussed in connection with FIGS. 1-6. Power transceiver 308 is coupled to camera control unit 310, which is used to receive and process image data from endoscope/camera 302 via the wireless coupling. It should be noted that endoscope/camera 302 is indicated a single unit in FIGS. 7-14A, however, it is contemplated that the camera may be detachable from the endoscope such that various cameras may be used with a single endoscope or various endoscopes may be used with a single camera.

Also shown in FIGS. 7 and 7A is a light source 306, which may comprise virtually any type of illuminating light source for use with the endoscope. The light source is shown coupled to a port 312 in the endoscope via an optical line 314. The port 312 is shown entering the endoscope at a right angle to a longitudinal axis of the endoscope shaft 316, however, it is contemplated that the port 312 could be provided at virtually any angle to provide illuminating light to the endoscope.

FIG. 7 shows device transceiver 304 coupled to endoscope/camera 302 with a doubled headed arrow indicating two-way communication. In one advantageous embodiment, the device transceiver 304 may be provided as a detachable module that can be attached to a camera to provide both electrical power to run the endoscope/camera 302 and provide a wireless data connection for transmission of endoscope/camera 302 information, control and command signals, and further function as an image data pathway. It is further contemplated that power transceiver 308 may also be provided as a detachable module such that, for example, the wireless power coupling arrangement may be retrofit and used with existing equipment. An alternate configuration is illustrated in FIG. 7A where the power transceiver 308 is provided inside and integral with camera control unit 310.

In both embodiments shown in FIGS. 7 and 7A, total electrical isolation between the patient and the source of electrical is provided as only the optical line 314 extends to the patient.

Figure 8:
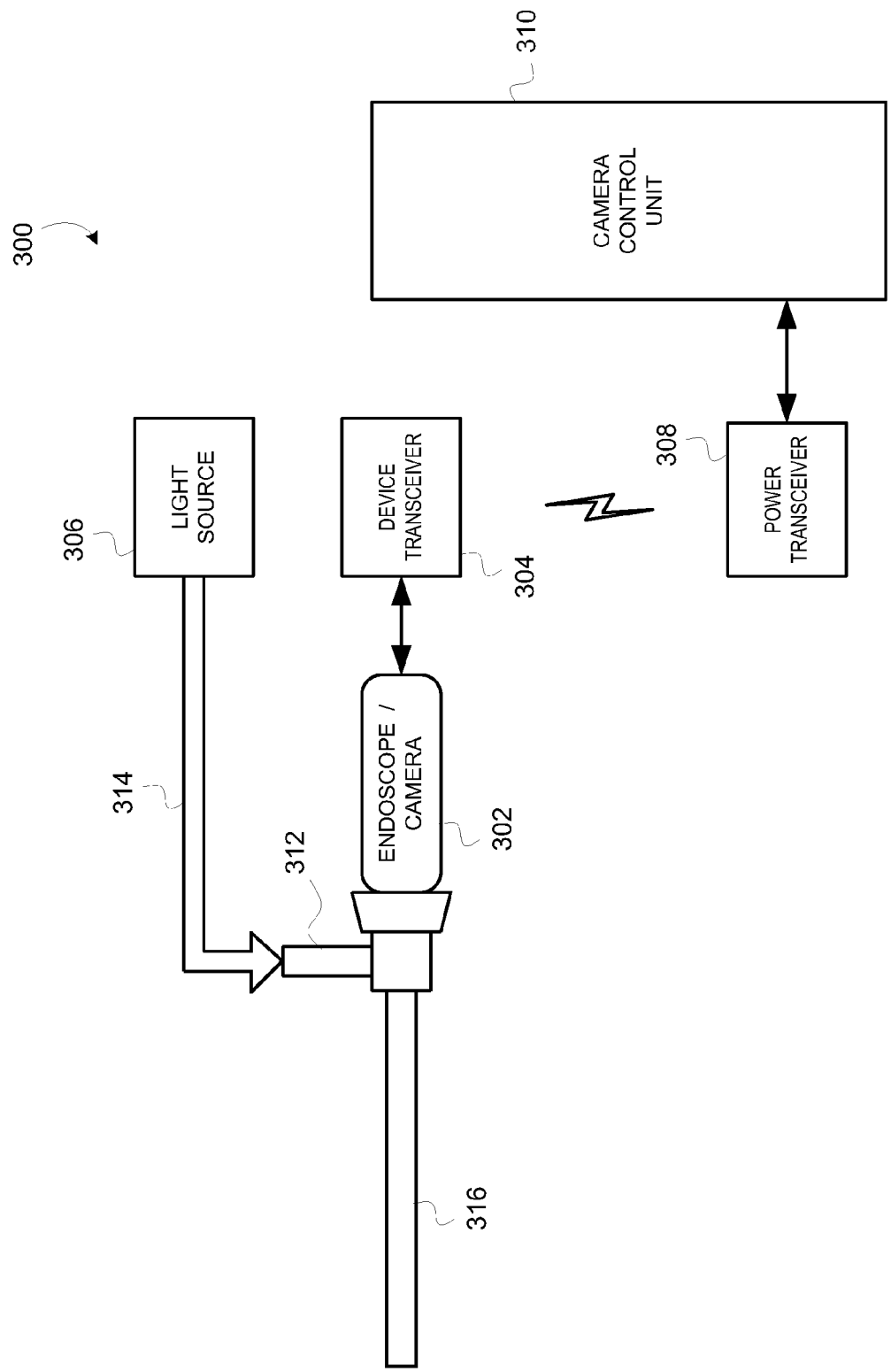
FIG. 8 is a block diagram according to the advantageous embodiment of 1.
Figure 8A:
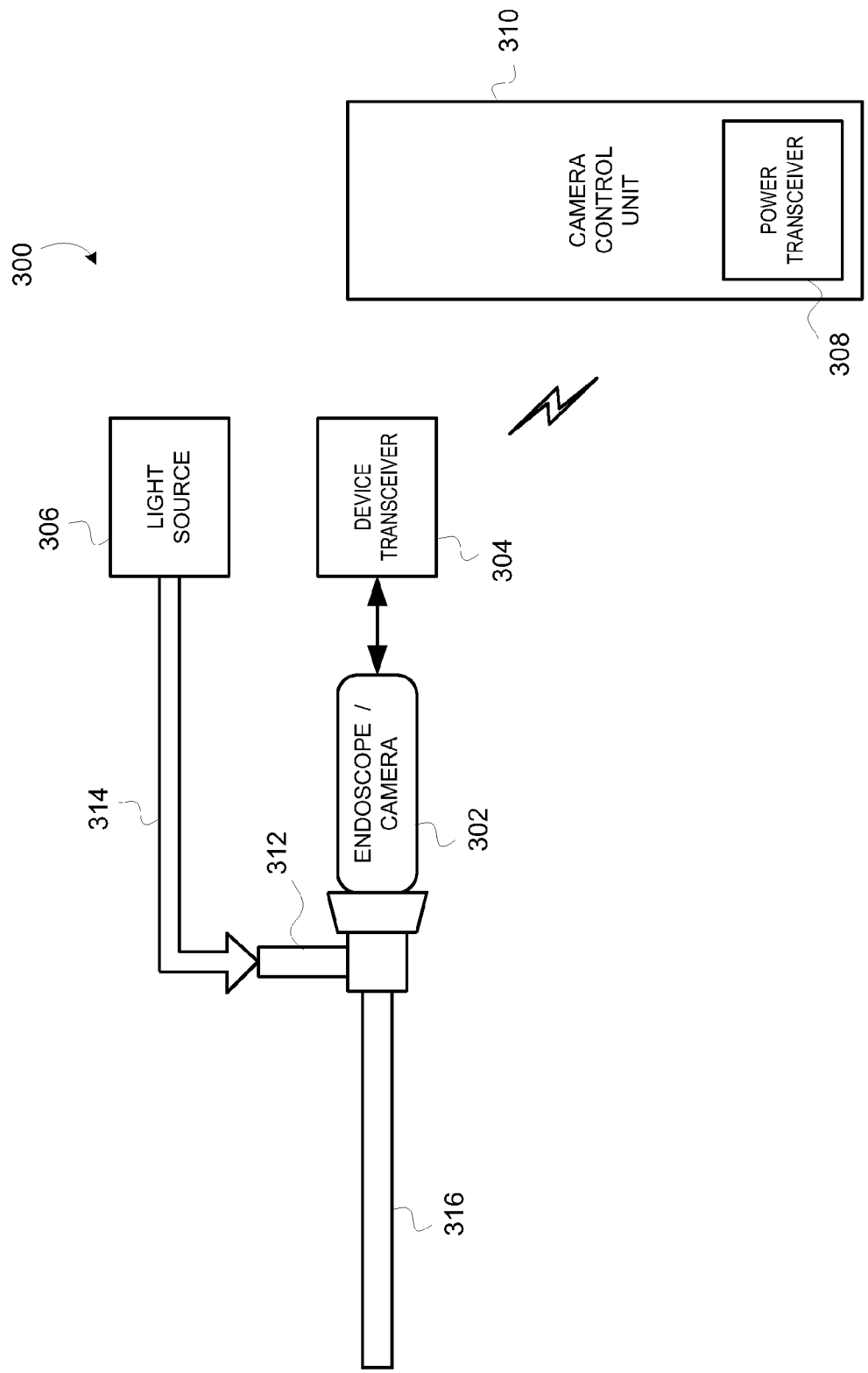
FIG. 8A is a block diagram according to the advantageous embodiment of 8.

FIGS. 8 and 8A are similar to the embodiments shown in FIGS. 7 and 7A except that the light source 306 is shown positioned in proximity to the endoscope/camera 302. For example, in FIGS. 7 and 7A, it is contemplated that the light source 306 may be provided as rack-mounted equipment adjacent to the camera control unit 310 and other equipment (not shown). However, in FIGS. 8 and 8A, it is contemplated that the light source 306 may be positioned in close proximity to the patient eliminating the optical line 314 from extending over a distance from, for example, the surgical rack to the patient.

Figure 9:
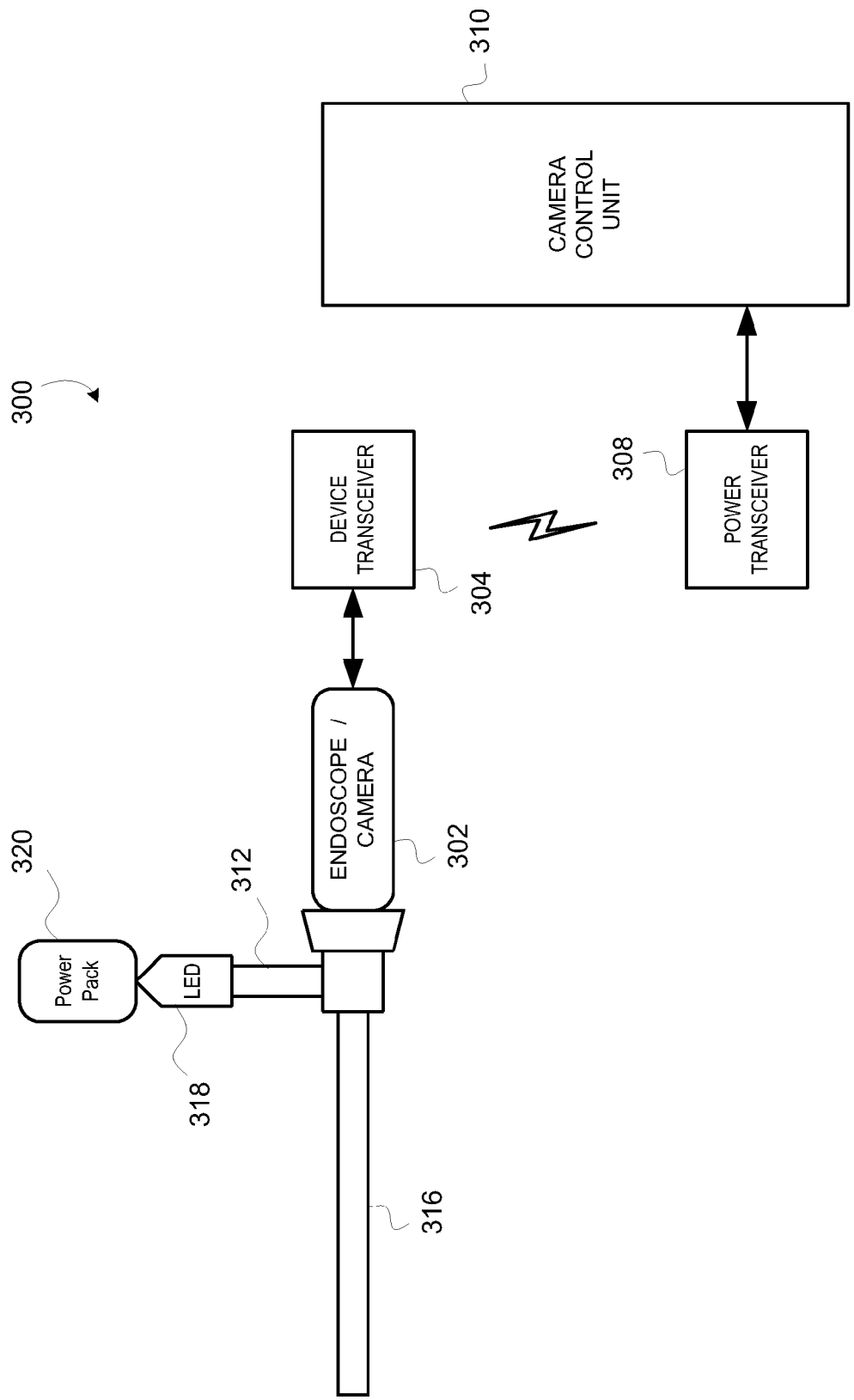
FIG. 9 is a block diagram according to the advantageous embodiment of 1.
Figure 9A:
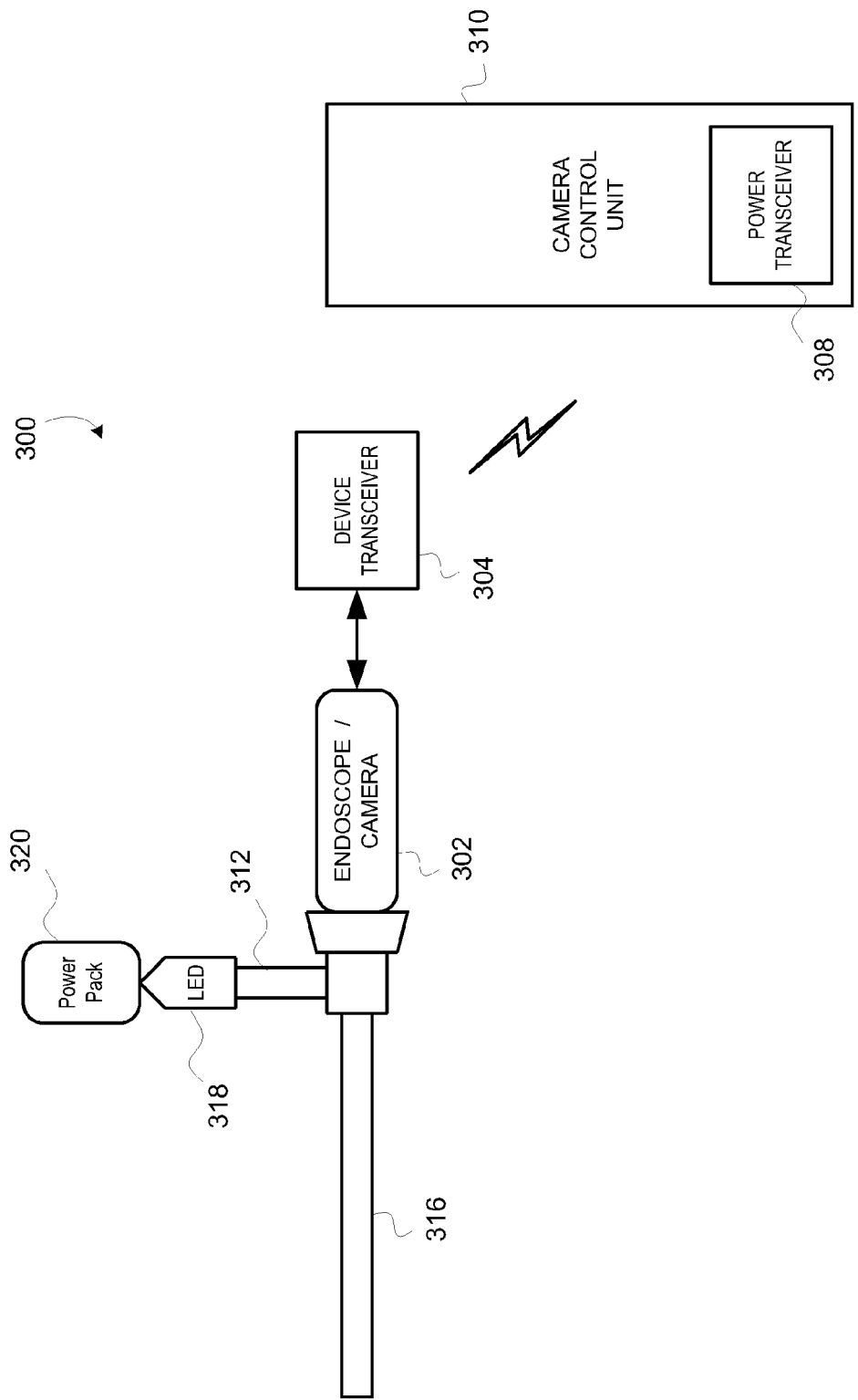
FIG. 9A is a block diagram according to the advantageous embodiment of 9.

FIGS. 9 and 9A are directed toward and embodiment where the light source comprises an LED 318 mounted on port 312 and a power pack 320 is coupled to the LED 318 to provide electrical power. In this embodiment, the LED 318 may be provided as a detachable illumination device. Likewise, power pack 320 may also be provided as a detachable, rechargeable power source. The device transceiver would still function as previously described, however, it would only provide power to the endoscope/camera as previously shown in FIGS. 7-8A. FIG. 9A is similar to FIG. 9 except that the power transceiver is provided inside and integral with camera control unit 310.

Figure 10:
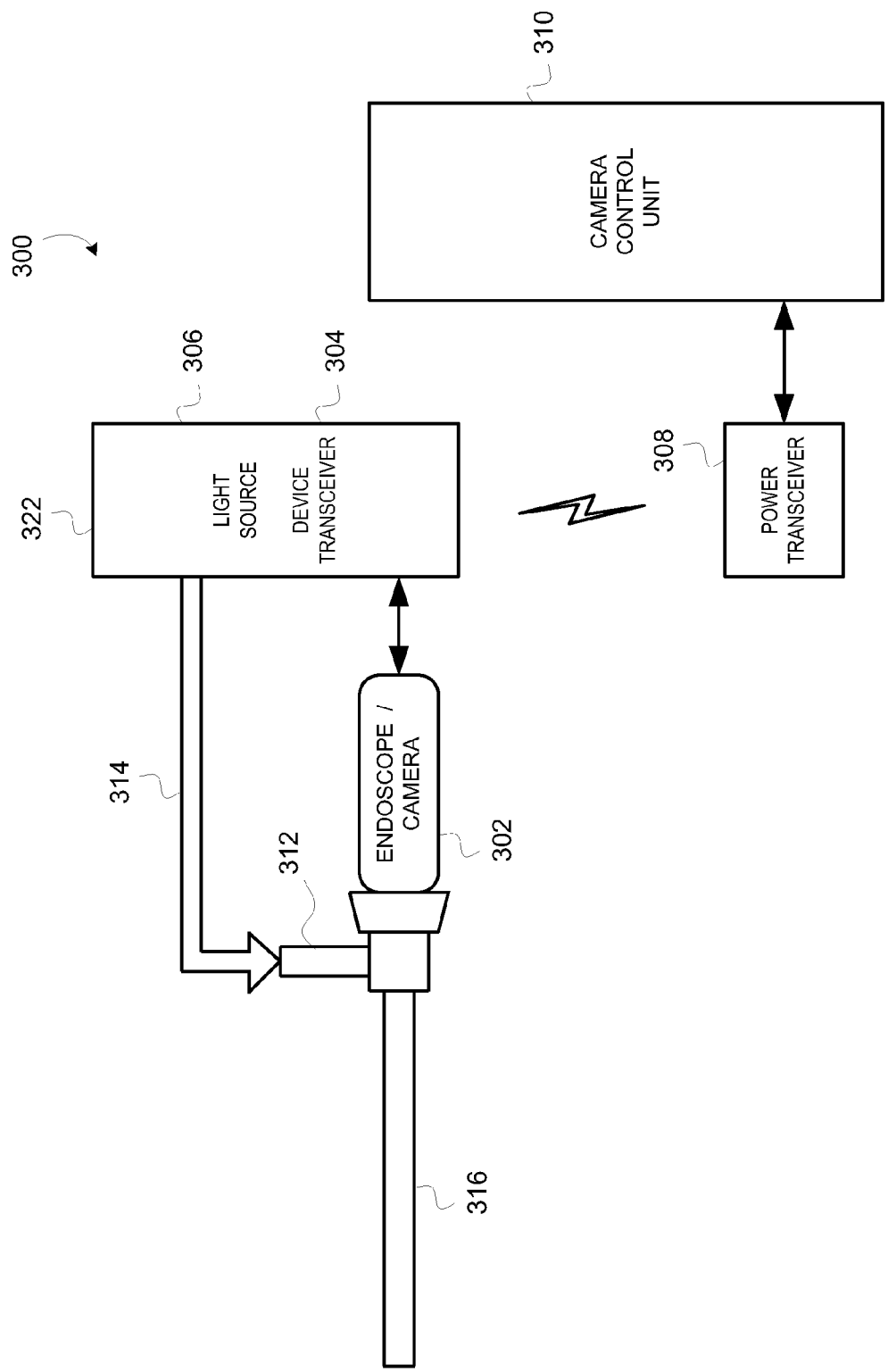
FIG. 10 is a block diagram according to the advantageous embodiment of 1.
Figure 10A:
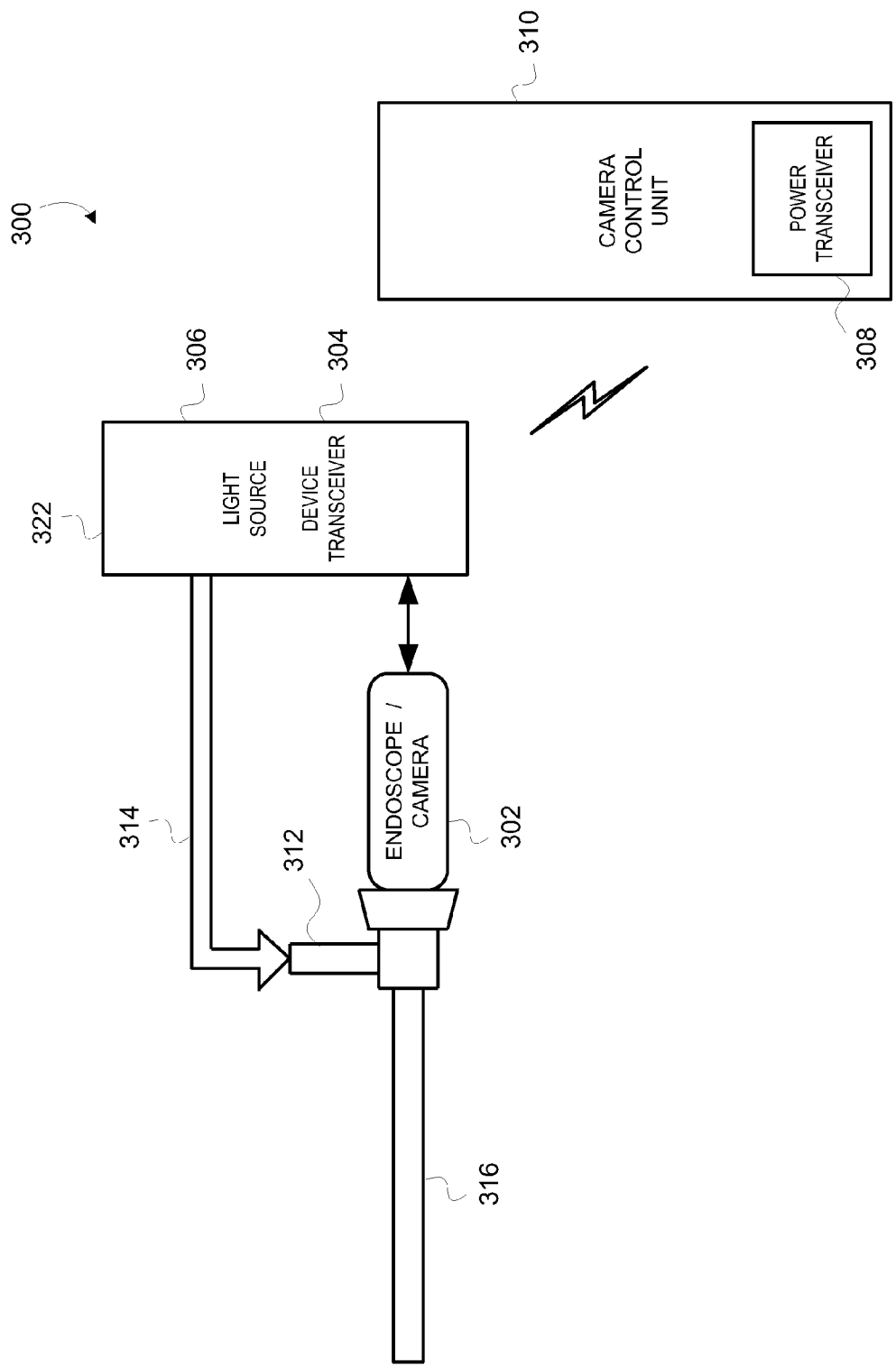
FIG. 10A is a block diagram according to the advantageous embodiment of 10.

FIGS. 10 and 10A illustrate still another embodiment where the device transceiver 304 is provided integral with light source 306 as a detachable module 322 that may be either positioned on the endoscope/camera 302. In this embodiment, it is contemplated that the device transceiver 304 may provide electrical power not only for endoscope/camera 302, but also for light source 306, which is provided with optical line 314 for connection to port 312. In this manner, module 322 including both device transceiver 304 and light source 306 may be used to, for example, retrofit with existing equipment. FIG. 10A is similar to FIG. 10 except that the power transceiver is provided inside and integral with camera control unit 310.

Figure 11:
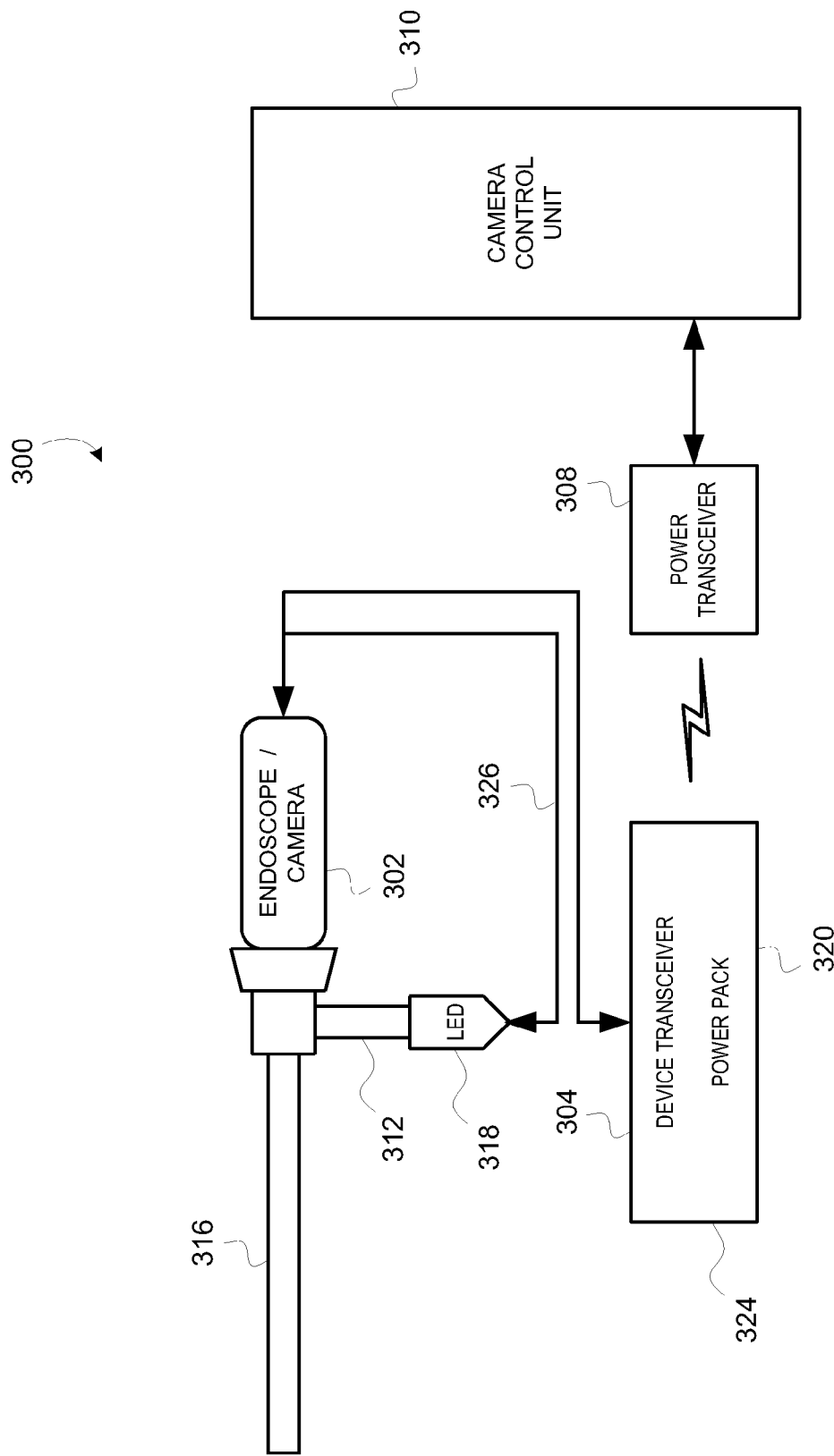
FIG. 11 is a block diagram according to the advantageous embodiment of 1.
Figure 11A:
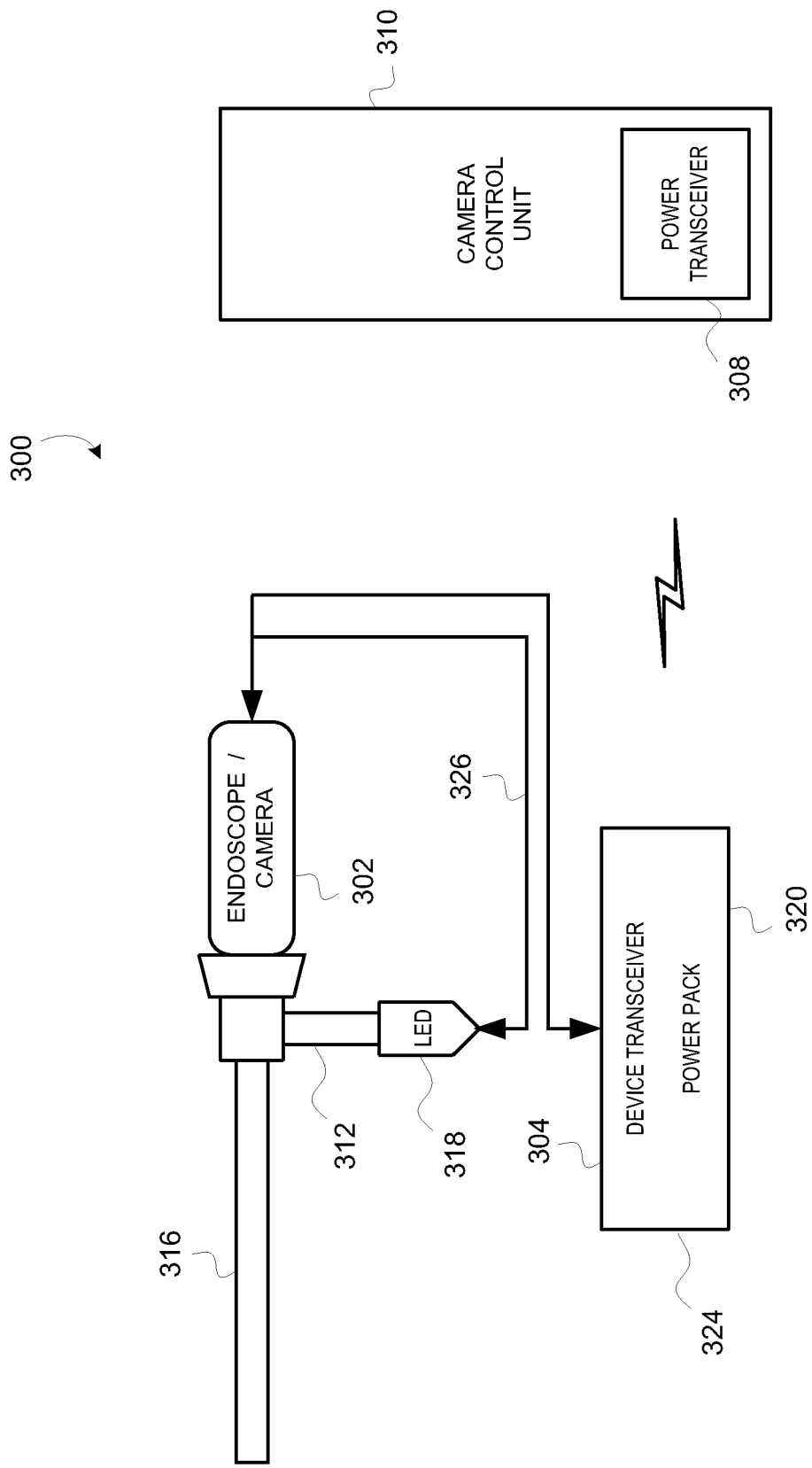
FIG. 11A is a block diagram according to the advantageous embodiment of 11.

FIGS. 11 and 11A illustrate yet another embodiment where the device transceiver 304 is provided integral with power pack 320 as a detachable module 324 that may be positioned on the endoscope/camera 302. In this embodiment, it is contemplated that the device transceiver 304 may provide electrical power not only for endoscope/camera 302, but also for LED 318, which is provided with line 326. In this manner, LED 318 and module 324 including both device transceiver 304 and power pack 320 may be used to, for example, retrofit with existing equipment. FIG. 11A is similar to FIG. 11 except that the power transceiver is provided inside and integral with camera control unit 310.

Figure 12:
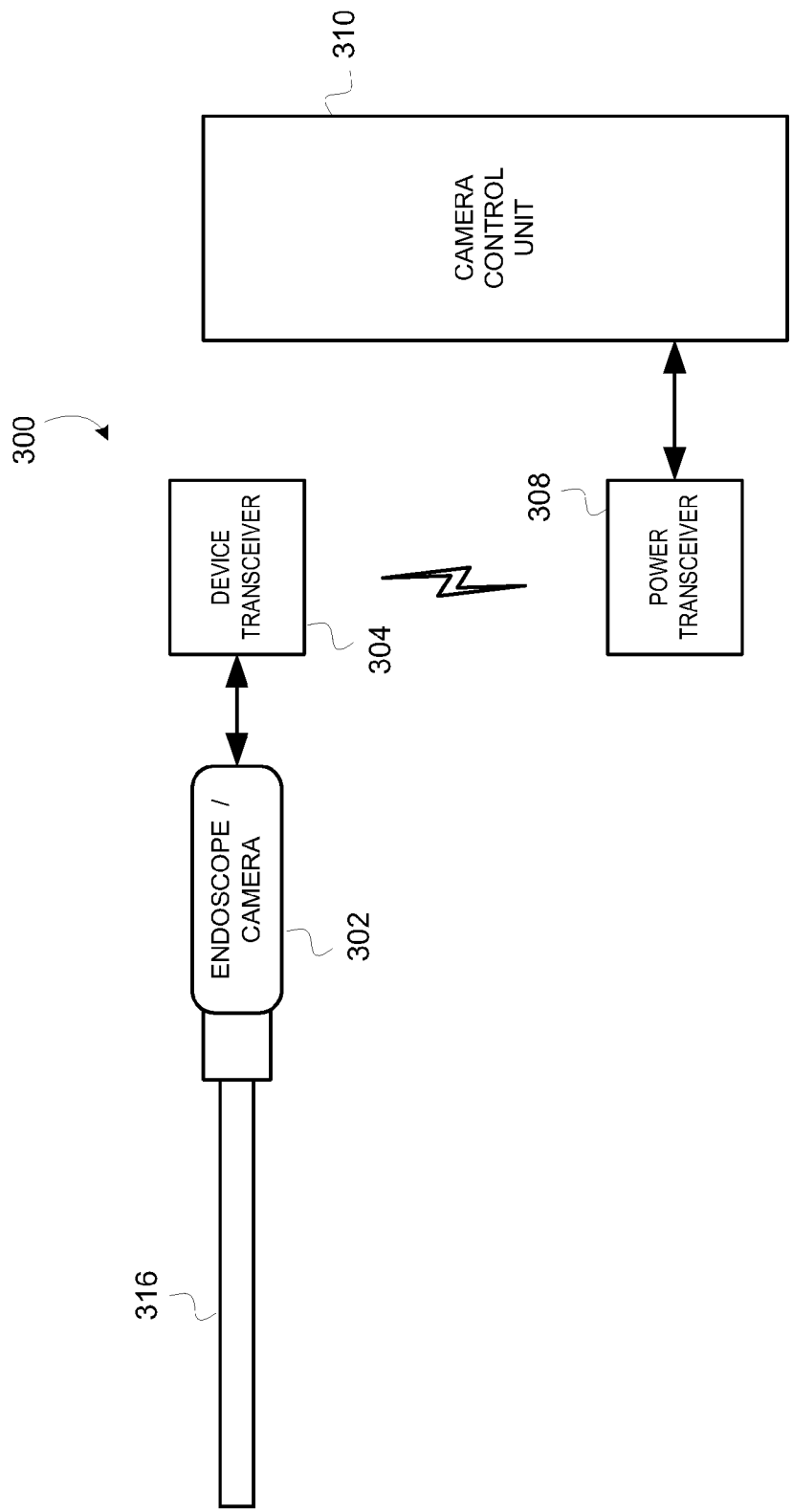
FIG. 12 is a block diagram according to the advantageous embodiment of 1.
Figure 12A:
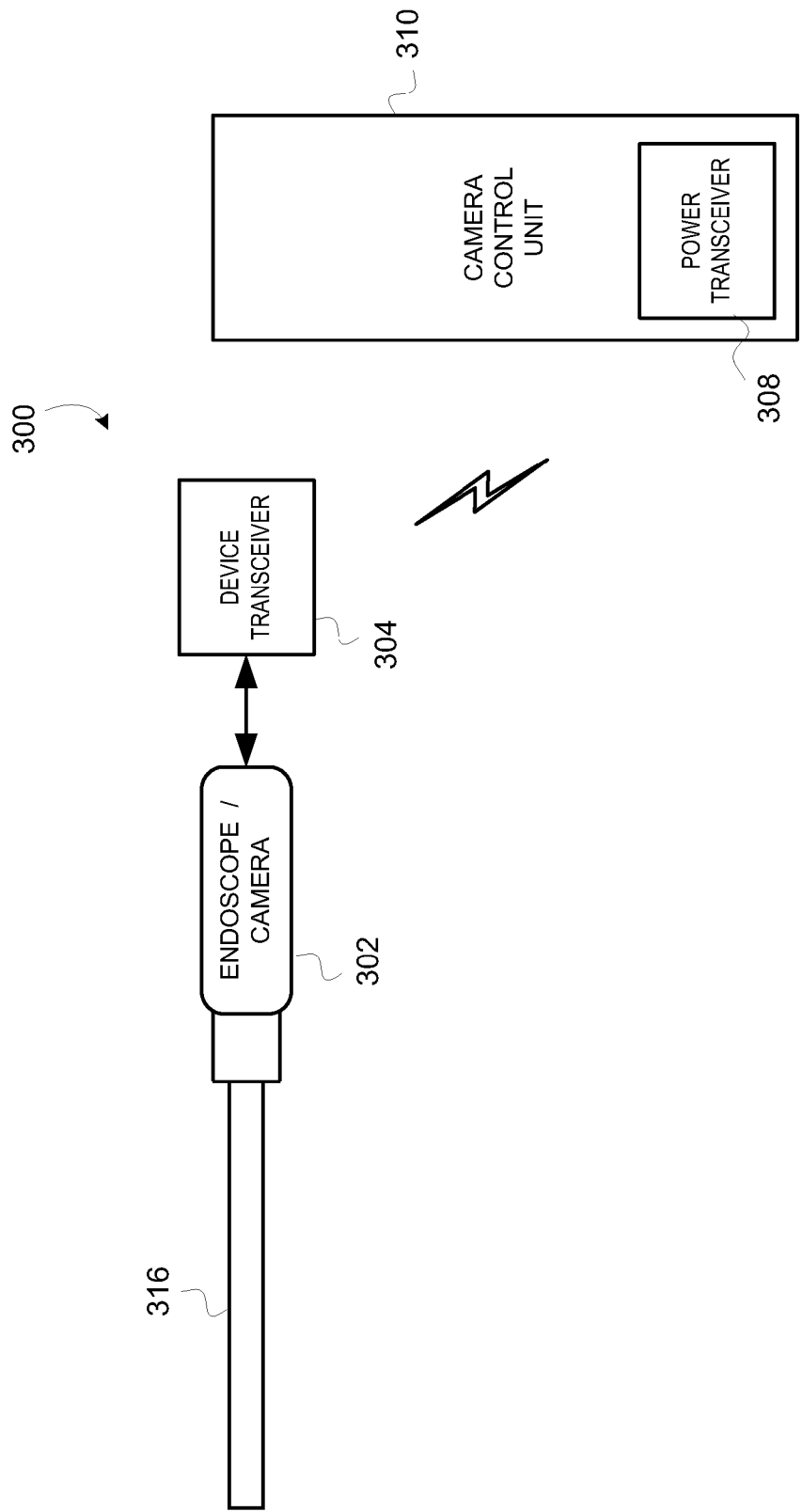
FIG. 12A is a block diagram according to the advantageous embodiment of 12.

FIGS. 12 and 12A substantially illustrate the systems disclosed in connection with FIGS. 7 and 7A, with the exception that light source 306 is no shown. This is because it is contemplated that the illuminating light is generated by a light source internal to the endoscope/camera 302. Accordingly, device transceiver 304 is provided to not only for the electrical circuitry of the endoscope and the camera, but also for the internal illuminating light source (not shown) thereby totally eliminating the need for cables. FIG. 12A is similar to FIG. 12 except that the power transceiver is provided inside and integral with camera control unit 310.

Figure 13A:
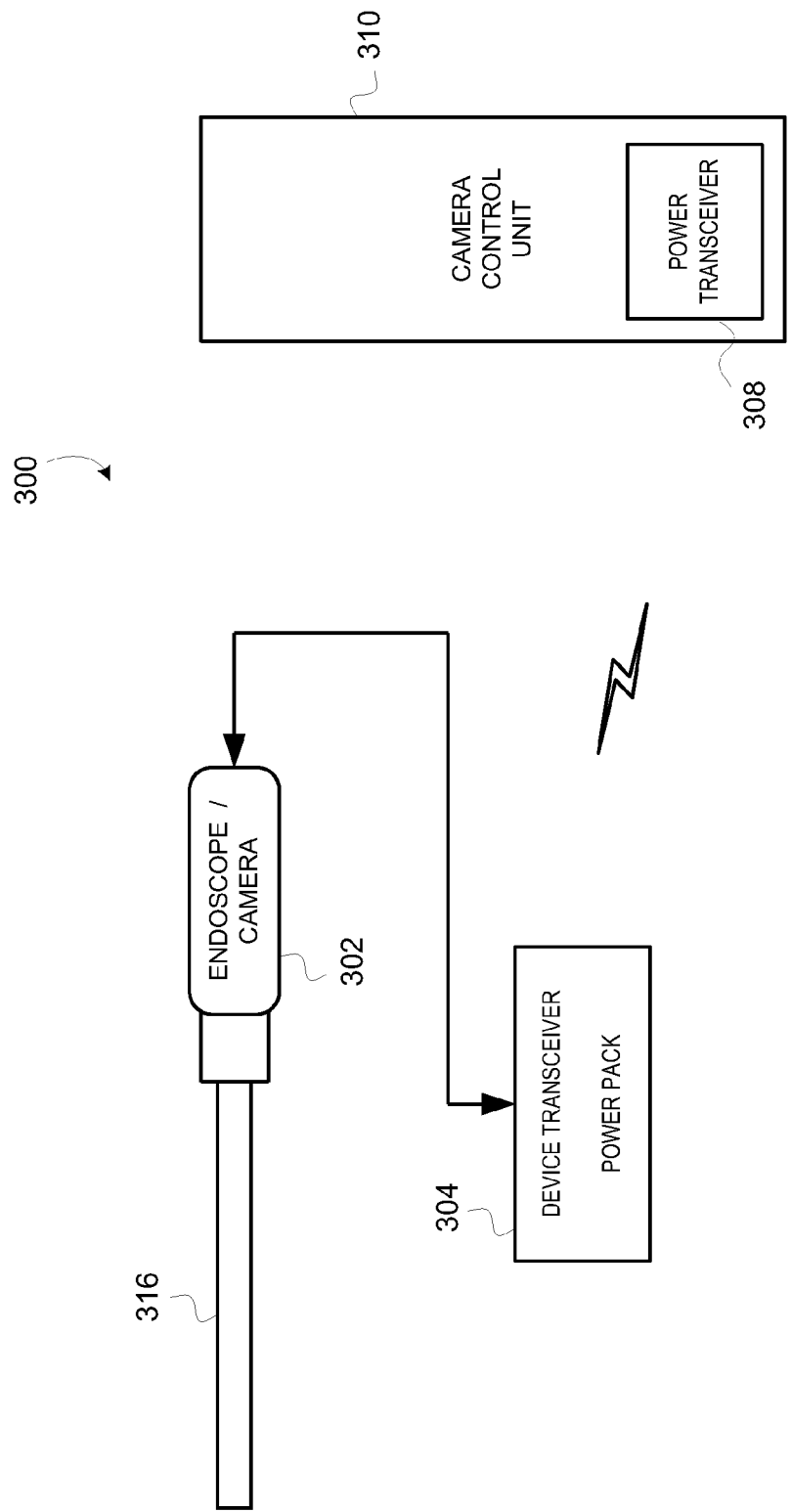
FIG. 13A is a block diagram according to the advantageous embodiment of 13.

FIGS. 13 and 13A is similar in function to FIGS. 11 and 11A where device transceiver 304 is provided integral with power pack 320 as a detachable module 324 that may be positioned on the endoscope/camera 302. In this embodiment, similar to FIGS. 12 and 12A, illuminating light is generated by a light source internal to the endoscope/camera 302. FIG. 13A is similar to FIG. 13 except that the power transceiver is provided inside and integral with camera control unit 310.

Figure 14A:
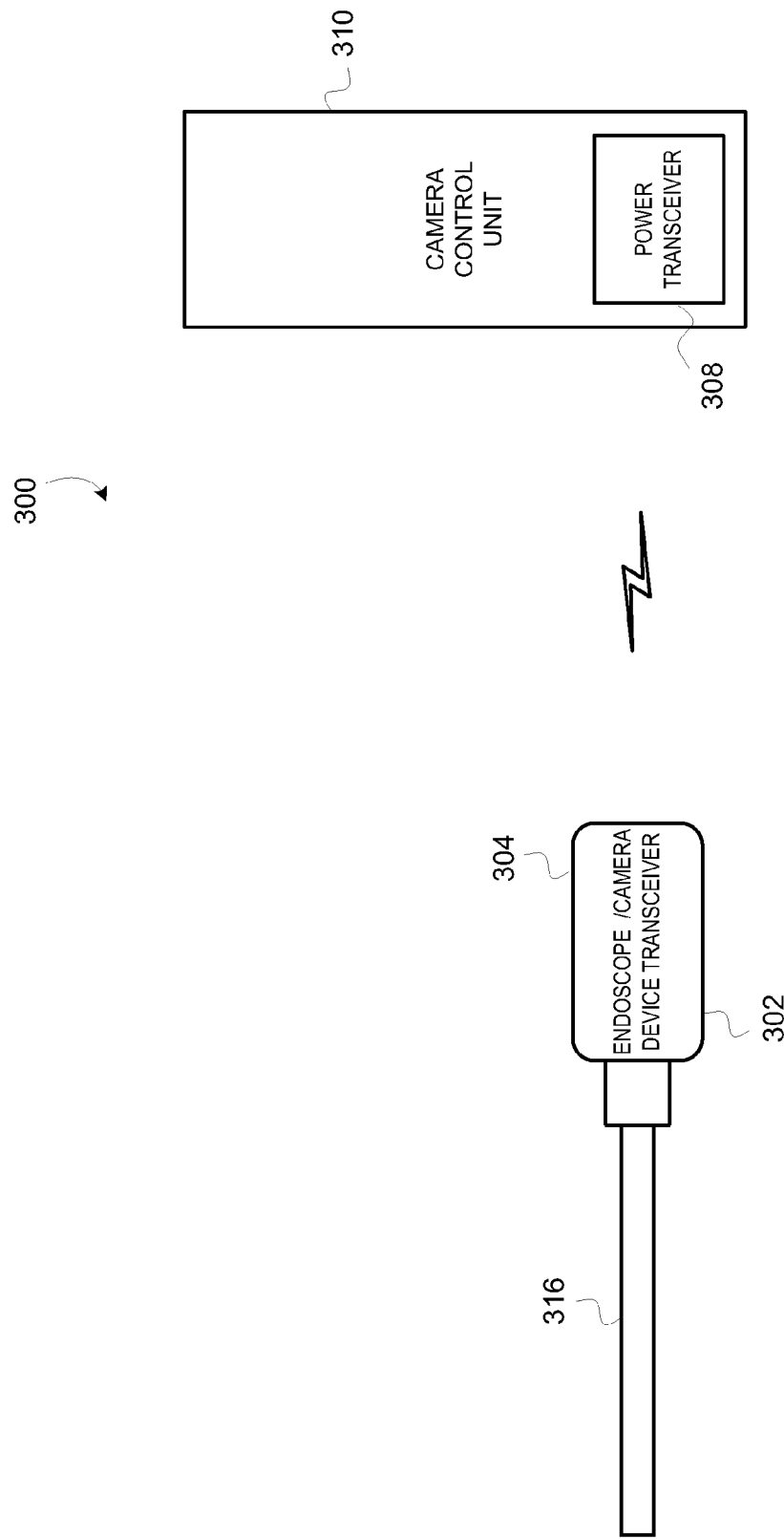
FIG. 14A is a block diagram according to the advantageous embodiment of 14.

FIGS. 14 and 14A illustrate a final embodiment where device transceiver 324 (not shown) is position in endoscope/camera 302 and function substantially in the same manner as previously described. Likewise, FIG. 14A depicts power transceiver 308 positioned inside of camera control unit 310.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An endoscope system comprising:
    an endoscope;
    a camera detachably coupled to said endoscope, said camera generating image data;
    a camera control unit;
    a device transceiver coupled to said camera when said camera is detachably coupled to said endoscope;
    a power transceiver coupled to said camera control unit;
    a light source generating illuminating light, said light source is positioned in said endoscope and coupled to said device transceiver;

said power transceiver generating a resonant magnetic field;

said device transceiver tuned to said resonant magnetic field such that resonant interaction occurs between said device transceiver and said power transceiver and power is transmitted to said device transceiver by said resonant interaction; and wherein electrical power is provided to said camera by said device transceiver such that said camera and said light source are powered by the electrical power transmitted to said device transceiver by said power transceiver; and wherein the image data from the camera is transmitted to the camera control unit by the device transceiver and power transceiver via said resonant interaction.

2. The endoscope system according to claim 1 further comprising a display coupled to said camera control unit, wherein said camera transmits the image data to said display via said camera control unit and said image data is presented on said display.

3. The endoscope system according to claim 1 wherein said camera control unit is coupled to a network.

4. The endoscope system according to claim 3 wherein said camera control unit is coupled to a surgical suite comprising at least one controller and at least one surgical tool in addition to said endoscope.

5. The endoscope system according to claim 1 wherein when said device transceiver is brought within a predefined radius of said power transceiver, said power transceiver and said device transceiver automatically wirelessly couple to each other.

6. The endoscope system according to claim 5 wherein when said power transceiver and said device transceiver couple to each other, said camera and said camera control unit automatically couple to each other such that said camera control unit automatically identifies said camera and automatically adjusts operational settings of said camera control unit based upon the identification.

7. The endoscope system according to claim 1 further comprising a power storage coupled to said device transceiver such that, in the event of an interruption in the wireless resonant coupling between said device transceiver and said power transceiver, said power storage provides electrical power to said camera.

8. The endoscope system according to claim 7 wherein when said device transceiver is wirelessly resonantly coupled to said power transceiver, said power storage charges.

9. The endoscope system according to claim 1 wherein said device transceiver is provided as a detachable module that is coupled to said camera.

10. The endoscope system according to claim 1 wherein said device transceiver is positioned in and is integral with said camera.

11. The endoscope system according to claim 1 wherein said power transceiver is provided as a detachable module that is coupled to said camera control unit.

12. The endoscope system according to claim 1 wherein said power transceiver is positioned in and is integral with said camera control unit.

13. The endoscope system according to claim 1 wherein said light source comprises an LED.

14. The endoscope system according to claim 13 further comprises a power storage coupled to said endoscope for providing electrical power to said LED.

15. The endoscope system according to claim 1 wherein said device transceiver is positioned in a module that is coupled to said endoscope.

16. The endoscope system according to claim 1 further comprising a power storage wherein said power storage and said device transceiver are positioned in a module that is coupled to said endoscope.

17. The endoscope system according to claim 1 wherein the resonant interaction comprises evanescent stationary near-field.

18. The endoscope system according to claim 1 wherein the device transceiver and power transceiver comprise dielectric disks and capacitively-loaded conducting-wire loops.

19. The endoscope system according to claim 1 wherein data transmitted by the device transmitter and power transmitter via said resonant coupling interaction includes camera identification data and control and command data.

20. A method for providing an endoscope system that comprises an endoscope, a camera and a camera control unit, the method comprising the steps of:

detachably coupling the camera to the endoscope;

coupling a device transceiver to the camera when the camera is detachably coupled to the endoscope;

coupling the device transceiver to a light source positioned on the endoscope;

coupling a power transceiver to the camera control unit;

generating a resonant magnetic field with the power transceiver;

coupling the device transceiver to the power transceiver, the device transceiver tuned to the resonant magnetic field generated by the power transceiver so that resonant interaction occurs between the device transceiver and the power transceiver;

transmitting power to the device transceiver from the power transmitter;

generating electrical power with the device transceiver;

providing electrical power from the device transceiver to the camera and the light source;

generating illuminating light with the light source;

transmitting the illuminating light to an area to be viewed;

receiving reflected light from the area to be viewed with the camera;

generating image data with the camera; and transmitting the image data from the camera to the camera control unit via the device transceiver and power transceiver.

21. The method according to claim 20 further comprising the steps of:

coupling a display to the camera control unit;

transmitting the image data to the display; and presenting the image data on the display.

22. The method according to claim 20 wherein the camera control unit is coupled to a network.

23. The method according to claim 22 wherein the camera control unit is coupled to a surgical suite that includes at least one controller and at least one surgical tool in addition to the endoscope.

24. The method according to claim 20 further comprising the steps of:

coupling a power storage to the device transceiver such that, in the event of an interruption in the wireless resonant coupling between the device transceiver and the power transceiver, the power storage provides electrical power to the camera.

25. The method according to claim 20 wherein the device transceiver is provided as a detachable module that is coupled to the camera.

26. The method according to claim 25 wherein the step of coupling the device transceiver to the camera comprises retrofitting an existing camera for use with the endoscope system.

27. The method according to claim 20 wherein the device transceiver is positioned in and is integral with the camera.

28. The method according to claim 20 wherein the power transceiver is provided as a detachable module that is coupled to the camera control unit.

29. The method according to claim 20 wherein the power transceiver is positioned in and is integral with the camera control unit.

30. The method according to claim 20 wherein the light source is an LED.

* * * * *